United States Patent
Peyton

(10) Patent No.: US 11,612,675 B1
(45) Date of Patent: Mar. 28, 2023

(54) FISH SKIN BIOLOGIC BANDAGE

(71) Applicant: The Regents of the University of California, Oakland, CA (US)

(72) Inventor: Jamie Peyton, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 917 days.

(21) Appl. No.: 16/456,517

(22) Filed: Jun. 28, 2019

Related U.S. Application Data

(60) Provisional application No. 62/691,439, filed on Jun. 28, 2018.

(51) Int. Cl.
| | |
|---|---|
| *A61L 27/36* | (2006.01) |
| *A61L 27/54* | (2006.01) |
| *A61L 27/60* | (2006.01) |
| *A61K 31/43* | (2006.01) |
| *A61K 35/60* | (2006.01) |
| *A61K 31/7048* | (2006.01) |

(52) U.S. Cl.
CPC .......... *A61L 27/3687* (2013.01); *A61K 31/43* (2013.01); *A61K 31/7048* (2013.01); *A61K 35/60* (2013.01); *A61L 27/362* (2013.01); *A61L 27/54* (2013.01); *A61L 27/60* (2013.01); *A61L 2300/204* (2013.01); *A61L 2300/232* (2013.01); *A61L 2300/30* (2013.01); *A61L 2300/406* (2013.01)

(58) Field of Classification Search
CPC .... A61L 27/3687; A61L 27/362; A61L 27/54; A61L 27/60; A61L 2300/204; A61L 2300/232; A61L 2300/30; A61L 2300/406; A61K 31/43; A61K 31/7048; A61K 35/60
See application file for complete search history.

(56) References Cited

U.S. PATENT DOCUMENTS

| | | |
|---|---|---|
| 8,613,957 B2 | 12/2013 | Sigurjonsson et al. |
| 2018/0272026 A1 | 9/2018 | Lima Junior et al. |

FOREIGN PATENT DOCUMENTS

| | | |
|---|---|---|
| WO | 2017/035615 A1 | 3/2017 |

OTHER PUBLICATIONS

Lima-Junior, E.M. et al., "Innovative treatment using tilapia skin as a xenograft for partial thickness burns after a gunpowder explosion," *Journal of Surgical Case Reports*, 2019, pp. 1-4, vol. 6.
Nunes Alves, A.P.N. et al., "Study of tensiometric properties, microbiological and collagen content in nile tilapia skin submitted to different sterilization methods," *Cell Tissue Bank*, 2018, pp. 373-382, vol. 19.
Brulliard, K.; "Two bears were badly burned in wildfires, and fish skin helped heal them"; *The Washington Post*: Jan. 26, 2018.

*Primary Examiner* — Kade Ariani
(74) *Attorney, Agent, or Firm* — Kilpatrick Townsend and Stockton LLP

(57) ABSTRACT

The invention is directed to a biological bandage derived from fish skin (e.g. tilapia skin) that can be used with healing of wounds such as burn wounds. The edible property of the fish skin biological bandage according to various embodiments makes it suitable for both human and veterinary medicine.

27 Claims, 7 Drawing Sheets

FIG. 7A
FIG. 7B
FIG. 7C
FIG. 7D
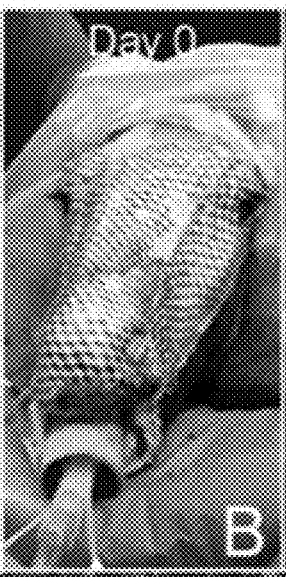
FIG. 7E
FIG. 7F

FISH SKIN BIOLOGIC BANDAGE

CROSS-REFERENCES TO RELATED APPLICATIONS

The present application claims priority to U.S. Provisional Patent Application No. 62/691,439, filed on Jun. 28, 2018, which application is incorporated herein by reference in its entirety.

BACKGROUND OF THE INVENTION

An ideal wound healing dressing should protect the wound from mechanical trauma, bacterial/fungal contamination, and provide a warm, moist healing environment. It is preferable to have biocompatible wound dressings that can promote cellular proliferation, migration, tissue remodeling, and other processes. Certain types severe tissue injuries, such as burns, pressure wounds, or delayed/non-healing wounds that do not heal despite adequate treatment, may require biologic dressings to promote advanced healing.

The standard of care for treating wounds in veterinary medicine is to apply non-adherent synthetic bandage material on the wound of an animal. However, such bandages are subject to ingestion or removal by the animal with the potential for subsequent gastrointestinal obstruction. Moreover, a synthetic bandage does not carry the inherent healing benefits of a biological bandage.

In human medicine, there are both natural and synthetic collagen matrix or dermal substitutes that may be used in healing of wounds. One type of collagen matrix is a xenograft, which is typically derived from porcine or bovine tissue. However, such xenografts carry a high risk of zoonotic diseases, such as prion disease, that can be transmitted to the patient through conventional animal-based xenografts. Conventional animal-based xenografts further carry the risk of immune reaction from the recipient patient. Conventional animal-based xenografts are also expensive to harvest, sterilize, and apply. Alternatively, non-viable skin grafts or allographs may be obtained from cadavers as skin substitute. However, such skin grafts are expensive to obtain and not readily available at large quantities. In addition, such skin grafts carry the risk of being rejected by the body of the recipient patient.

In wildlife, injured animal patients are difficult to keep in captivity for the standard recovery time due to fear of habituation and risk of further injury during confinement. Traditional medications and bandages are also more challenging to administer and apply due to the need for anesthesia and the risk of bandage ingestion resulting in gastrointestinal obstruction. Accordingly, there is a need for biological bandages and methods for preparing said bandages. The present disclosure provides these and other needs.

BRIEF SUMMARY OF THE INVENTION

In general, provided herein are methods for preparing a biological bandage derived from fish skin (e.g. tilapia skin) that can be used with healing of wounds such as burn wounds. The edible property of the fish skin biological bandage according to the disclosure herein is suitable for both human and veterinary medicine.

In one aspect, the present disclosure provides a method for preparing a fish skin biological bandage. The method involves the steps of: i) harvesting fish skin from a fish; ii) statically immersing the fish skin in a disinfectant solution for a first predetermined amount of time; iii) contacting the fish skin with a first rinse solution; iv) statically immersing the fish skin in a first dehydration solution for a second predetermined amount of time; v) statically immersing the fish skin in a second dehydration solution at a predetermined temperature for a third predetermined amount of time; vi) statically immersing the fish skin in a second rinse solution for a fourth predetermined amount of time; vii) statically immersing the fish skin in a treatment solution at the predetermined temperature for a fifth predetermined amount of time to form a processed fish skin; and viii) packaging the processed fish skin in a sealed package.

In some embodiments, the disinfectant solution comprises chlorhexidine, wherein the chlorhexidine is present in an amount ranging from about 0.1% to about 3.0% (w/v). In some embodiments, the first predetermined amount of time and the second predetermined amount of time is about 120 minutes or less. In some embodiments, the first rinse solution and the second rinse solution comprise saline, wherein the saline is present in an amount ranging from about 0.25% to about 8.0% (w/v). In some embodiments, in step iii), contacting the fish skin with the first rinse solution comprises: a) rinsing the fish skin with the first rinse solution; and/or b) statically immersing the fish skin in the first rinse solution.

In some embodiments, the first dehydration solution comprises a mixture of a glycerol solution and a saline solution at a volume ratio of 75/25, wherein the glycerol solution comprises from about 80% to about 100% (w/v) glycerol and the saline solution comprises from about 0.25% to about 8.0% (w/v) saline. In some embodiments, the second dehydration solution comprises glycerol, wherein the glycerol is present in an amount of about 80% (w/v) or more. In some embodiments, the predetermined temperature ranges from about 2° C. to about 8° C. In some embodiments, the third predetermined amount of time is about 48 hours or less. In some embodiments, the fourth predetermined amount of time is about 30 minutes or less. In some embodiments, the fifth predetermined amount of time is about 24 hours or more.

In some embodiments, the treatment solution comprises glycerol and at least one antibiotic compound, wherein the glycerol is present in an amount of about 70% (w/v) or more and the at least one antibiotic compound is present in an amount ranging from about 0.01% to about 30% (w/v). In some embodiments, the at least one antibiotic compound is selected from the group comprising penicillin, streptomycin, or mixtures thereof.

In some embodiments, the processed fish skin is packaged in the sealed package, wherein the sealed package comprises about 40 mL to about 80 mL of a storage solution. In some embodiments, the storage solution is selected from the group comprising glycerol, at least one antibiotic compound, ethanol, peracetic acid, or mixtures thereof.

In some embodiments, the fish skin is harvested within 24 hours of death of the fish. In some embodiments, the fish is selected from the group comprising salmon, tuna, tilapia, or trout.

In some embodiments, the method further comprises repeating the steps of: ii) statically immersing the fish skin in a disinfectant solution for a first predetermined amount of time; and iii) contacting the fish skin with a first rinse solution, wherein steps ii) and iii) are repeated at least once and before performing step iv).

In some embodiments, the method further comprises at least one of the following additional steps: a) dynamically immersing the fish skin for at least 30 minutes in the disinfectant solution after step ii); b) dynamically immersing the fish skin for at least 30 minutes in the first rinse solution after step iii); c) dynamically immersing the fish skin for at least 30 minutes in the first dehydration solution after step iv); d) dynamically immersing the fish skin for at least 30 minutes in the second dehydration solution after step v); e) dynamically immersing the fish skin for at least 30 minutes in the second rinse solution after step vi); and/or f) dynamically immersing the processed fish skin for at least 30 minutes in the treatment solution after step vii).

In one aspect, the present disclosure provides a fish skin biological bandage prepared to the method described above.

In one aspect, the present disclosure provides a method for preparing a fish skin biological bandage. The method involves the steps of: i) harvesting fish skin from a fish; ii) statically immersing the fish skin in a disinfectant solution comprising about 0.5% to about 2.0% (w/v) chlorhexidine for about 60 minutes or less; iii) contacting the fish skin with a first rinse solution comprising about 0.45% to about 7.2% (w/v) saline; iv) statically immersing the fish skin in a first dehydration solution comprising a mixture of a glycerol solution and a saline solution at a volume ratio of 75/25 for 60 minutes or less, wherein the glycerol solution comprises about 80% to about 99.5% (w/v) glycerol and the saline solution comprises from about 0.45% to about 7.2% (w/v) saline; v) statically immersing the fish skin in a second dehydration solution comprising about 80% to about 99.5% (w/v) glycerol at 4° C. for about 24 hours; vi) statically immersing the fish skin in a second rinse solution comprising about 0.45% to about 7.2% (w/v) saline for about 15 minutes or less; vii) statically immersing the fish skin in a treatment solution comprising about 80% to about 99.9% (w/v) glycerol and about 0.1% to about 20% (w/v) penicillin and streptomycin at 4° C. for at least 24 hours to form a processed fish skin; and viii) packaging the processed fish skin in an individual vacuum sealed package, wherein the package comprises 80 mL or less of a storage solution comprising glycerol, at least one antibiotic compound, ethanol, peracetic acid, or mixtures thereof.

BRIEF DESCRIPTION OF THE DRAWINGS

FIGS. 7A-7F shows images of a gypsy cob pony with full thickness chemical burns to the face: at day 0, post debridement (FIG. 7A) and after placement of the processed tilapia skin biological bandage on the debrided burn (FIG. 7B); at day three (FIG. 7C) and at day six (FIG. 7D), showing new areas of tan colored epithelialization with residual processed tilapia skin biological bandages still attached to facilitate healing; at day 120 (FIG. 7E and FIG. 7F), showing full healing with new hair growth.

DETAILED DESCRIPTION OF THE INVENTION

The present disclosure relates to methods for preparing a biological bandage derived from fish skin (e.g. tilapia skin) that can be used to help with healing hard-healing or non-healing wounds, providing a source for a xenograft. The fish skin biological bandages prepared using the methods described herein have less immune reactivity than conventional xenografts, such as porcine or bovine derived xenografts. The biological bandage prepared using the methods described herein allow for the use of the entire skin of the fish, while conventional xenografts or other dermal substitutes must be covered by additional dressings.

The tough nature of the fish skin provides protection for wounds and can be utilized in areas where bandages cannot be applied. From a veterinary prospective, the edible property of the fish skin biological bandages reduces the risk of foreign body ingestion and gastrointestinal obstruction when used in animals. Inventors noted improved pain control compared to conventional bandage material. The fish skin biological bandage prepared using the methods described herein provides a collagen matrix to assist with enhanced epithelialization, decreases inflammation, and has antimicrobial effects.

The fish skin biological bandages described herein have several advantages over conventional wound dressings. The fish skin biological bandages prepared using the methods described herein provide protection due to its strong structure, and can be utilized in patients that may ingest their bandages (e.g. veterinary medicine applications). The fish skin biological bandages also provide enhanced pain control, by acting as a "secondary skin" to cover exposed nerve ends, and by decreasing inflammation. In addition, the treated skin covered with the fish skin biological bandage retains moisture, which is difficult to do with traditional dressings. The increased moisture promotes an ideal environment for wound healing. The fish skin also provides a collagen matrix, which is lacking in standard wound dressings. This matrix helps wound healing by providing a scaffold for epithelialization.

Another advantage of the fish skin biological bandage prepared according to the methods described herein is the decreased risk of zoonotic diseases, which can be transmitted to the recipient patient and the decreased potential for immune reaction from the patient. In addition, one advantage of the fish skin biological bandage is the decreased cost in comparison to conventional substitutes. This allows more veterinary and other lower income areas to have access to the improved and more efficient wound care.

Figure 1:
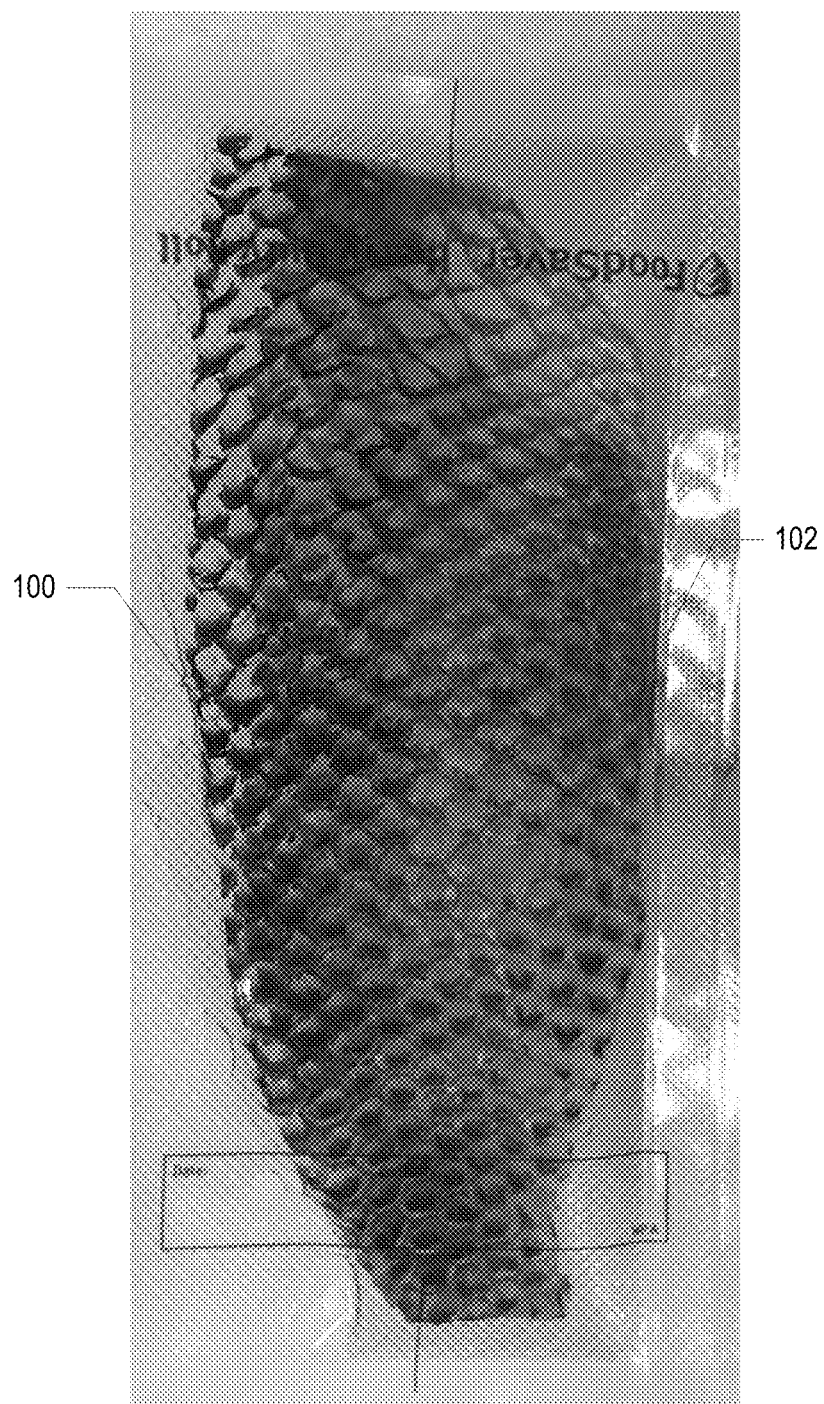
FIG. 1 illustrates an exemplary fish skin bandage packaged in a sealed packaging in accordance with embodiments of the disclosure.
Figure 2:
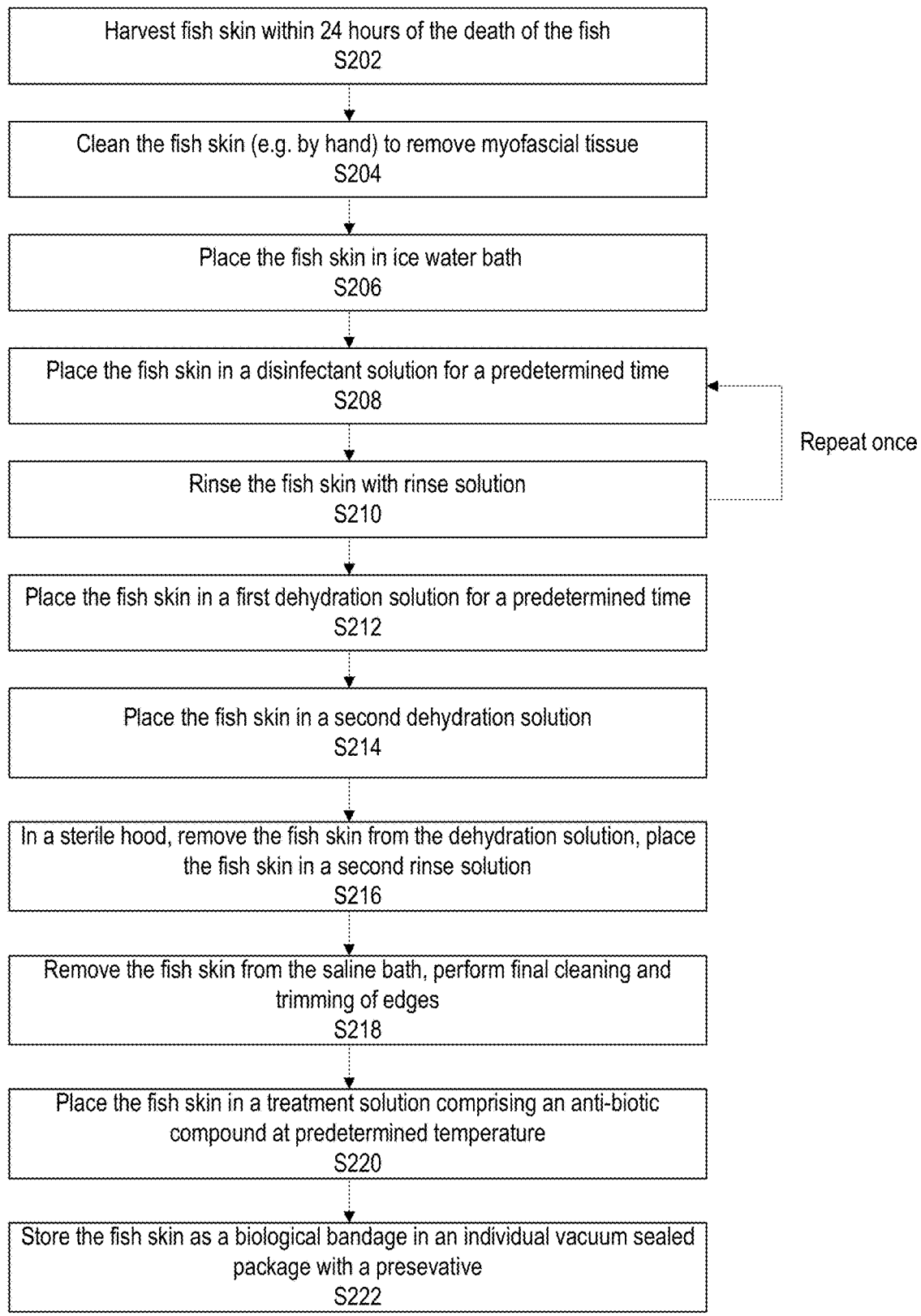
FIG. 2 illustrates an exemplary method for preparing a fish skin dressing in accordance with embodiments of the disclosure.

FIG. 1 illustrates an exemplary fish skin bandage 100 stored in a vacuum sealed packaging 102 according to various embodiments. An exemplary process for preparing the fish skin biological bandage 100 is illustrated in FIG. 2. The specific details describing the steps of the method shown in FIG. 2 are illustrative of only one embodiment of the invention. The order of certain steps can be changed as needed. Certain steps may also be repeated as necessary, while other steps may be omitted. Additional steps not illustrated in FIG. 2 may be included in the method for preparing the biological fish skin bandage, as described herein.

I. PREPARATION OF THE FISH SKIN BIOLOGICAL BANDAGE

A fish skin biological bandage is prepared in accordance with the method of the instant disclosure. The method for preparing the fish skin biological bandage comprises i) harvesting fish skin from a fish; ii) statically immersing the fish skin in a disinfectant solution for a first predetermined amount of time; iii) contacting the fish skin with a first rinse solution; iv) statically immersing the fish skin in a first dehydration solution for a second predetermined amount of time; v) statically immersing the fish skin in a second dehydration solution at a predetermined temperature for a third predetermined amount of time; vi) statically immersing the fish skin in a second rinse solution for a fourth predetermined amount of time; vii) statically immersing the fish skin in a treatment solution at the predetermined temperature for a fifth predetermined amount of time to form a processed fish skin; and viii) packaging the processed fish skin in a sealed package.

In some embodiments, a fish skin is harvested or obtained from a deceased fish. In some embodiments, the fish skin is harvested within no more than 48 hours of the death of the fish. In some embodiments, the fish skin is harvested within 48 to 24 hours of the death of the fish. For example, step S202 of FIG. 2 shows that the fish skin is harvested within 24 hours of the death of the fish. In general, it is preferable to harvest the fish skin as close as possible to the time of death of the fish to prevent bacterial infestation of the harvested skin. As such, in some embodiments, the fish skin is harvested within 24 hours of the death of the fish, or within 22 hours, 20, 18, 16, 14, 12, 10, 8, 6, 4, 3, 2, or within 1 hour of the death of the fish. In some embodiments, the fish skin is harvested within 12 hours of the death of the fish. In some embodiments, the fish skin is harvested within 6 hours of the death of the fish. In some embodiments, the fish skin is harvested within 4 hours of the death of the fish.

Suitable fish species for use as the source of fish skin in accordance with the methods described herein include bony or cartilaginous fish, or any fish classified as Osteichthyes (e.g., Actinopterygii, Chondrostei, Sarcopterygii, etc.), Chondrichthyes (e.g., Elasmobranchii, Holocephali, etc.), or Agnatha (e.g., Myxini, Hyperoartia, etc.). For example, the fish skin can be harvested from salmon, tuna, tilapia, swordfish, cod, sablefish, whitefish, hoki fish, smelt, haddock, whiting, pollock, catfish, mahi-mahi, flatfish, flounder, sole, turbot, plaice, halibut, trout, herring, sardine, pilchard, mackerel, anchovy, sturgeon, paddlefish, reedfish, bichir, lungfish, sharks, rays, skates, sawfish, chimaera, ratfish, lamprey, or hagfish. In some embodiments, the fish skin is harvested from a fish selected from the group comprising salmon, sturgeon, lamprey, tilapia, pilchards, tuna, herring, cod, sardines, mackerel, sablefish, smelts, whitefish, hoki fish, or trout. In some embodiments, the fish skin is harvested from a fish selected from the group comprising salmon, sturgeon, lamprey, tilapia, tuna, or trout. In some embodiments, the fish skin is harvested from sturgeon or tilapia. In some embodiments, the fish skin is harvested from sturgeon. In some embodiments, the fish skin is harvested from tilapia.

The fish skin can be harvested from any suitably sized area of the fish. In some embodiments, the fish skin is removed from the fish by first incising around the margins of each side of the fish. The skin is then removed from the fish in one or more continuous pieces using traction or a dermatome. The removed skin is then placed in an ice bath (or cool or cold environment) at a temperature between −4° C. and 10° C. for about 1 minute to about 90 minutes (e.g., 5 minutes, 10, 15, 20, 25, 30 minutes, etc.) In some embodiments, the skin is cleaned by hand to ensure removal of myofascial tissue (step S204) before placing in the ice water bath (step S206). In some embodiments, the skin is cleaned by hand to ensure removal of myofascial tissue (step S204) after placing in the ice water bath (step S206).

After harvesting the fish skin from a fish, the fish skin is contacted with various solutions for particular amounts of time. As used herein, the terms "contacting," "contacted," or "contact" refer to the process of bringing into contact at least two distinct species such that they are touching or of immediate or local proximity (i.e., the application of a solution to the fish skin). In the context of the instant disclosure, contacting includes the application of a solution to a portion of the fish skin at a time, such as rinsing or washing; and the application of a solution to the entire fish skin at once, such as immersion. A fish skin that is immersed in a solution is a fish skin that is completely covered by the solution. In some embodiments, immersion may be static, in which the fish skin is covered by the solution and is not moved (e.g., soaking). In other embodiments, immersion is dynamic, which includes covering the fish skin with a solution while imparting shaking, rocking, sonication, or other mild movement on the fish skin while it is immersed. Dynamic immersion, such as rocking or shaking, will be slow and gentle compared to centrifuging. In fact, the methods described herein specifically exclude steps which involve subjecting the fish skins to any kind of vigorous agitation, such as, for example, stirring or centrifuging (especially stirring or centrifuging at 15 revolutions per minute (RPM) or more), mechanical or manual massaging, ultrasonication (>20 kHz), and pressure. By subjecting the fish skins to only mild rocking or shaking, trauma to the fish skin is minimized and the collagen structure is maintained.

In some embodiments, the harvested fish skin is statically immersed in a disinfectant solution for a first predetermined amount of time (step S208). In some embodiments, the disinfectant solution comprises an antimicrobial and/or antiseptic agent, such as, for example, polyhexamethylene biguanide (PHMB, also known as polihexanide), triclosan, octenidine, PVP-iodine, chlorhexidine (chlorhexidine digluconate), silver, hypochlorus acid, sodium hypochlorite, and any combination thereof. In some embodiments, the disinfectant solution comprises PHMB, triclosan, octenidine, chlorhexidine, or mixtures thereof. In some embodiments, the disinfectant solution comprises chlorhexidine.

In some embodiments, the disinfectant solution comprises an antimicrobial and/or antiseptic agent (e.g., chlorhexidine) in an amount ranging from about 0.1% to about 3.0% (w/v). In some embodiments, the disinfectant solution comprises about 0.1% (w/v) of an antimicrobial and/or antiseptic agent, or about 0.2%, about 0.3%, about 0.5%, 0.8%, 1.0%, 1.25%, 1.5%, 1.75%, 2.0%, 2.25%, 2.50%, 2.75%, or about 3.0% (w/v) of an antimicrobial and/or antiseptic agent. In some embodiments, the disinfectant solution comprises from about 0.5% to about 2.5% (w/v) of an antimicrobial and/or antiseptic agent. In some embodiments, the disinfectant solution comprises from about 0.5% to about 2.0% (w/v) of an antimicrobial and/or antiseptic agent. In some embodiments, the disinfectant solution comprises from about 1.0% to about 2.0% (w/v) of an antimicrobial and/or antiseptic agent. In some embodiments, the disinfectant solution comprises about 2.0% (w/v) of an antimicrobial and/or antiseptic agent. In some embodiments, the disinfectant solution comprises about 2.0% (w/v) of chlorhexidine.

In some embodiments, the first predetermined amount of time is about 120 minutes or less. In some embodiments, the first predetermined amount of time is about 120 minutes, or about 110 minutes, about 100 minutes, 90, 80, 75, 70, 60, 50, 45, 40, 30, 25, 20, 15, 10, or about 5 minutes. In some embodiments, the first predetermined amount of time is about 90 minutes or less. In some embodiments, the first predetermined amount of time is about 60 minutes or less. In some embodiments, the first predetermined amount of time is about 30 minutes.

After statically immersing the fish skin in a disinfectant solution for a first predetermined amount of time, the fish skin is contacted with a first rinse solution (step S210). In some embodiments, contacting the fish skin with a first rinse solution comprises rinsing the fish skin with the first rinse solution and/or statically immersing the fish skin in the first rinse solution. In some embodiments, contacting the fish skin with a first rinse solution comprises rinsing the fish skin with the first rinse solution. The fish skin is rinsed with a first rinse solution for any suitable amount of time, such as, for example, 30 minutes, 25, 20, 15, 10, 5, 4, 3, 2, about 1 minute, or any ranges or fractional values between these.

In some embodiments, the first rinse solution comprises saline in an amount ranging from about 0.25% to about 8.0% (w/v). As used herein, the term "saline" refers to salt, and more particularly, to sodium chloride. In some embodiments, the first rinse solution comprises about 0.25% (w/v) of saline, or about 0.3%, 0.35%, 0.4%, 0.45%, 0.5%, 0.55%, 0.6%, 0.65%, 0.7%, 0.75%, 0.8%, 0.85%, 0.9%, 1.0%, 1.5%, 1.8%, 2.0%, 2.2%, 2.5%, 2.8%, 3.0%, 3.5%, 4.0%, 4.2%, 4.5%, 4.8%, 5.0%, 5.2%, 5.5%, 5.8%, 6.0%, 6.2%, 6.5%, 6.8%, 7.0%, 7.2%, 7.5%, or about 8.0% (w/v) of saline. In some embodiments, the first rinse solution comprises saline in an amount ranging from about 0.45% to about 7.2% (w/v). In some embodiments, the first rinse solution comprises saline in an amount ranging from about 0.5% to about 5.5% (w/v). In some embodiments, the first rinse solution comprises saline in an amount ranging from about 0.75% to about 3.8% (w/v). In some embodiments, the first rinse solution comprises about 0.9% (w/v) of saline.

In some embodiments, the first rinse solution is a buffered saline solution. In some embodiments, the buffered saline solution has a pH ranging from between about 5.5 to about 7.6 (e.g., a pH of about 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, or any ranges or fractional values between these). In some embodiments, the buffered saline solution contains a biocompatible buffer, such as, for example, citrate buffer, a phosphate buffer, an acetate buffer; HEPES buffer, MOPS buffer, Tris buffer, a combination of a citrate buffer and a phosphate buffer (citrate/phosphate buffer), or any other biocompatible buffers known in the art. The buffer can be at a concentration of up to 150 mM (e.g., 1, 5, 10, 15, 20, 25, 30, 35, 50, 55, 60, 65, 70, 75, 80, 85, 90, 95, 100, 110, 115, 120, 125, 130, 135, 140, 145, 150, or any ranges or fractional values between these) mM in the solution.

In some embodiments, the method further comprises repeating steps S208 and S210 at least once again. In other words, the steps of ii) statically immersing the fish skin in a disinfectant solution for a first predetermined amount of time; and iii) contacting the fish skin with a first rinse solution, are repeated at least once again before proceeding to step iv) of the method. That is, each piece of fish skin is again statically immersed in the disinfectant solution (e.g. 2.0% (w/v) chlorhexidine) for less than 120 minutes. Thereafter, each piece of skin is again contacted with the first rinse solution (e.g. 0.9% (w/v) saline).

Following the completion of the disinfecting and rinsing steps, each piece of fish skin is statically immersed in a first dehydration solution for a second predetermined amount of time (step S212). In some embodiments, the first dehydration solution comprises a mixture of a glycerol solution and a saline solution at a volume ratio. As used herein, the term "volume ratio" refers to the relation between the volume of a first component and the volume of a second component within a solution. For example, in the context of the instant disclosure, a first dehydration solution may contain a mixture of glycerol solution and saline solution at a volume ratio of 90/10, wherein 90 refers to the volume of the glycerol solution (i.e., first component) and 10 refers to the volume of the saline solution (i.e., second component).

In some embodiments, the mixture of the glycerol solution and the saline solution of the first dehydration solution can be a mixture of any suitable volume ratio, such as, for example, 95/5 (e.g., 95 mL glycerol solution and 5 mL saline solution), or 90/10, 85/15, 80/20, 75/25, 70/30, 65/35, or 60/40. In some embodiments, the first dehydration solution comprises a mixture of a glycerol solution and a saline solution at a volume ratio of 95/5, 90/10, 85/15, 80/20, 75/25, or 70/30. In some embodiments, the first dehydration solution comprises a mixture of a glycerol solution and a saline solution at a volume ratio of 95/5, 90/10, 85/15, 80/20, or 75/25. In some embodiments, the first dehydration solution comprises a mixture of a glycerol solution and a saline solution at a volume ratio of 75/25.

In some embodiments, the glycerol solution of the first dehydration solution comprises from about 80% to about 100% (w/v) glycerol. In some embodiments, the glycerol solution of the first dehydration solution comprises from about 80% (w/v) glycerol, or about 82%, about 84%, about 86%, 88%, 90%, 91%, 92%, 93%, 94%, 95%, 96%, 97%, 98%, 99%, or about 100% (w/v) of glycerol. In some embodiments, the glycerol solution of the first dehydration solution comprises from about 80% to about 99.9% (w/v) of glycerol. In some embodiments, the glycerol solution of the first dehydration solution comprises from about 80% to about 99.5% (w/v) of glycerol. In some embodiments, the glycerol solution of the first dehydration solution comprises from about 99.5% (w/v) of glycerol.

In some embodiments, the saline solution of the first dehydration solution comprises saline in an amount ranging from about 0.25% to about 8.0% (w/v). In some embodiments, the saline solution of the first dehydration solution comprises about 0.25% (w/v) of saline, or about 0.3%, 0.35%, 0.4%, 0.45%, 0.5%, 0.55%, 0.6%, 0.65%, 0.7%, 0.75%, 0.8%, 0.85%, 0.9%, 1.0%, 1.5%, 1.8%, 2.0%, 2.2%, 2.5%, 2.8%, 3.0%, 3.5%, 4.0%, 4.2%, 4.5%, 4.8%, 5.0%, 5.2%, 5.5%, 5.8%, 6.0%, 6.2%, 6.5%, 6.8%, 7.0%, 7.2%, 7.5%, or about 8.0% (w/v) of saline. In some embodiments, the saline solution of the first dehydration solution comprises from about 0.45% to about 7.2% (w/v) of saline. In some embodiments, the saline solution of the first dehydration solution comprises from about 0.5% to about 5.5% (w/v) of saline. In some embodiments, the saline solution of the first dehydration solution comprises from about 0.75% to about 3.8% (w/v) of saline. In some embodiments, the saline solution of the first dehydration solution comprises about 0.9% (w/v) of saline. In some embodiments, the saline solution of the first dehydration solution is a buffered saline solution, as described above.

In some embodiments, the second predetermined amount of time is about 120 minutes or less. In some embodiments, the second predetermined amount of time is about 120 minutes, or about 110 minutes, about 100 minutes, 90, 80, 75, 70, 60, 50, 45, 40, 30, 25, 20, 15, 10, or about 5 minutes. In some embodiments, the second predetermined amount of time is about 90 minutes or less. In some embodiments, the second predetermined amount of time is about 60 minutes or less. In some embodiments, the second predetermined amount of time is about 30 minutes.

In some embodiments, the fish skin is statically immersed in a first dehydration solution comprising a mixture of a glycerol solution and a saline solution at a volume ratio of 75/25 for 60 minutes or less, wherein the glycerol solution comprises about 80% to about 99.5% (w/v) glycerol and the saline solution comprises from about 0.45% to about 7.2% (w/v) saline. In some embodiments, the fish skin is statically immersed in a pre-dehydration solution comprising a mixture of a glycerol solution and a saline solution at a volume ratio of 50/50 for 60 minutes or less, followed by statically immersing the fish skin in a first dehydration solution comprising a mixture of a glycerol solution and a saline solution at a volume ratio of 75/25 for 60 minutes or less, wherein the glycerol solution comprises about 80% to about 99.5% (w/v) glycerol and the saline solution comprises from about 0.45% to about 7.2% (w/v) saline. The high percentage of glycerol in the first dehydration solution is intentionally used to pull the water out of the fish skin and to kill bacteria in the fish skin. The saline component of the solution reduces the shock to the fish skin coming from a 2% chlorhexidine solution immersion and 0.9% saline rinsing.

In some embodiments, instead of statically immersing the fish skin in a first dehydration solution for a second predetermined amount of time, the fish skin may be preserved via cryopreservation, the details of which are provided herein.

After statically immersing the fish skin in a first dehydration solution for a second predetermined amount of time, the fish skin is then statically immersed in a second dehydration solution at a predetermined temperature for a third predetermined amount of time (step S214). In some embodiments, the second dehydration solution comprises from about 80% to about 100% (w/v) glycerol. In some embodiments, the second dehydration solution comprises from about 80% (w/v) glycerol, or about 82%, about 84%, about 86%, 88%, 90%, 91%, 92%, 93%, 94%, 95%, 96%, 97%, 98%, 99%, or about 100% (w/v) of glycerol. In some embodiments, the second dehydration solution comprises from about 80% to about 99.9% (w/v) of glycerol. In some embodiments, the second dehydration solution comprises from about 80% to about 99.5% (w/v) of glycerol. In some embodiments, the second dehydration solution comprises from about 99.5% (w/v) of glycerol.

In some embodiments, the predetermined temperature ranges from about 2° C. to about 8° C. In some embodiments, the predetermined temperature is about 2° C., 3° C., 4° C., 5° C., 6° C., 7° C., or about 8° C. In some embodiments, the predetermined temperature is about 4° C.

In some embodiments, the third predetermined amount of time is about 48 hours or less. In some embodiments, the third predetermined amount of time is about 48 hours, or about 45 hours, or about 40, 36, 30, 24, 18, 12, 6, 4, 2, or 1 hour. In some embodiments, the third predetermined amount of time ranges from about 36 hours to about 24 hours or less. In some embodiments, the third predetermined amount of time is about 24 hours.

After statically immersing the fish skin in a second dehydration solution at a predetermined temperature for a third predetermined amount of time, the fish skin is then statically immersed in a second rinse solution for a fourth predetermined amount of time (step S216). In some embodiments, the fish skin is statically immersed in a second rinse solution while in a sterile environment. As used herein, the term "sterile environment" refers to an environment where greater than 99% of living germs and/or microorganisms have been removed (for example, a laminar hood).

In some embodiments, the second rinse solution comprises saline in an amount ranging from about 0.25% to about 8.0% (w/v). In some embodiments, the second rinse solution comprises about 0.25% (w/v) of saline, or about 0.3%, 0.35%, 0.4%, 0.45%, 0.5%, 0.55%, 0.6%, 0.65%, 0.7%, 0.75%, 0.8%, 0.85%, 0.9%, 1.0%, 1.5%, 1.8%, 2.0%, 2.2%, 2.5%, 2.8%, 3.0%, 3.5%, 4.0%, 4.2%, 4.5%, 4.8%, 5.0%, 5.2%, 5.5%, 5.8%, 6.0%, 6.2%, 6.5%, 6.8%, 7.0%, 7.2%, 7.5%, or about 8.0% (w/v) of saline. In some embodiments, the second rinse solution comprises from about 0.45% to about 7.2% (w/v) of saline. In some embodiments, the second rinse solution comprises from about 0.5% to about 5.5% (w/v) of saline. In some embodiments, the second rinse solution comprises from about 0.75% to about 3.8% (w/v) of saline. In some embodiments, the second rinse solution comprises about 0.9% (w/v) of saline. In some embodiments, the second rinse solution is a buffered saline solution, as described above.

In some embodiments, the fourth predetermined amount of time is about 90 minutes or less. In some embodiments, the fourth predetermined amount of time is about 90 minutes, or about 80 minutes, about 70 minutes, 60, 50, 45, 40, 35, 30, 29, 28, 27, 26, 25, 24, 23, 22, 21, 20, 19, 18, 17, 16, 15, 14, 13, 12, 11, 10, 9, 8, 7, 6, 5, 4, 3, 2, or about 1 minute. In some embodiments, the fourth predetermined amount of time ranges from about 90 minutes to about 1 minute. In some embodiments, the fourth predetermined amount of time ranges from about 60 minutes to about 5 minutes. In some embodiments, the fourth predetermined amount of time ranges from about 45 minutes to about 7 minutes. In some embodiments, the fourth predetermined amount of time ranges from about 30 minutes to about 10 minutes. In some embodiments, the fourth predetermined amount of time is about 60 minutes or less. In some embodiments, the fourth predetermined amount of time is about 30 minutes or less. In some embodiments, the fourth predetermined amount of time is about 15 minutes or less. In some embodiments, the fourth predetermined amount of time is about 15 minutes. In some embodiments, the fourth predetermined amount of time ranges from about 15 minutes to about 1 minute.

In some embodiments, after statically immersing the fish skin in a second rinse solution for a fourth predetermined amount of time, the fish skin can be removed from the second rinse solution to be cleaned by hand again and to trim the edges of the skin (step S218).

After statically immersing the fish skin in a second rinse solution for a fourth predetermined amount of time, the fish skin is then statically immersed in a treatment solution at the predetermined temperature for a fifth predetermined amount of time to form a processed fish skin (step S220). In some embodiments, the treatment solution comprises glycerol and/or glycol (e.g., ethylene glycol, propylene glycol, etc.), and at least one antibiotic compound. In some embodiments, the treatment solution comprises glycol (e.g., ethylene glycol, propylene glycol, etc.) and at least one antibiotic compound. In some embodiments, the treatment solution comprises glycerol and at least one antibiotic compound. Suitable antibiotic compounds for use in the treatment solution include penicillin, vancomycin, streptomycin, gentamycin, kanamycin, amikacin, arbekacin, netilmicin, tobramycin, neomycin, bacitracin, clindamycin, daptomycin, lincomycin, linezolid, metronidazole, polymyxin, rifaximin, cephalosporin, cefazolin, cefalexin, erythromycin, azithromycin, ciprofloxacin, levofloxacin, sulfadiazine, minocycline, tetracycline, rifampin, XF antibiotics, teixobactin, teixobactin analogues, oritavacin, dalbavancin, tedizolid, antibacterial synthetic retinoids, or mixtures thereof. In some embodiments, the at least one antibiotic compound of the treatment solution is selected from the group comprising penicillin, vancomycin, streptomycin, gentamycin, kanamycin, neomycin, or mixtures thereof. In some embodiments, the at least one antibiotic compound of the treatment solution is selected from the group comprising penicillin, streptomycin, or mixtures thereof.

In some embodiments, the treatment solution comprises from about 70% (w/v) or more glycol (e.g., ethylene glycol, propylene glycol, etc.). In some embodiments, the treatment solution comprises from about 70% (w/v) or more glycerol. In some embodiments, the treatment solution comprises from about 70% to about 100% (w/v) of glycol. In some embodiments, the treatment solution comprises from about 70% to about 100% (w/v) of glycerol. In some embodiments, the treatment solution comprises from about 70% to about 99.99% (w/v) of glycol. In some embodiments, the treatment solution comprises from about 70% to about 99.99% (w/v) of glycerol. In some embodiments, the treatment solution comprises from about 70% (w/v) of glycol, or about 72%, about 74%, about 76%, 78%, 80%, 82%, 84%, 86%, 88%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or about 99.99% (w/v) of glycol. In some embodiments, the treatment solution comprises from about 70% (w/v) of glycerol, or about 72%, about 74%, about 76%, 78%, 80%, 82%, 84%, 86%, 88%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or about 99.99% (w/v) of glycerol. In some embodiments, the treatment solution comprises from about 80% to about 99.9% (w/v) of glycol. In some embodiments, the treatment solution comprises from about 80% to about 99.9% (w/v) of glycerol. In some embodiments, the treatment solution comprises from about 80% to about 99.5% (w/v) of glycol. In some embodiments, the treatment solution comprises from about 80% to about 99.5% (w/v) of glycerol. In some embodiments, the treatment solution comprises from about 99.5% (w/v) of glycol. In some embodiments, the treatment solution comprises from about 99.5% (w/v) of glycerol.

In some embodiments, the treatment solution comprises from about 0.01% to about 30% (w/v) of at least one antibiotic compound. In some embodiments, the treatment solution comprises from about 0.01% (w/v) of at least one antibiotic compound, or about 0.025%, 0.05%, 0.075%, 0.1%, 0.25%, 0.3%, 0.35%, 0.4%, 0.45%, 0.5%, 0.55%, 0.6%, 0.65%, 0.7%, 0.75%, 0.8%, 0.85%, 0.9%, 1.0%, 1.5%, 2.0%, 2.5%, 3.0%, 3.5%, 4.0%, 4.5%, 5.0%, 5.5%, 6.0%, 7.0%, 7.5%, 8.0%, 8.5%, 9.0%, 9.5%, 10%, 12%, 15%, 18%, 20%, 22%, 25%, or about 30.0% (w/v) of at least one antibiotic compound. In some embodiments, the treatment solution comprises from about 0.01% to about 20% (w/v) of at least one antibiotic compound. In some embodiments, the treatment solution comprises from about 0.05% to about 10% (w/v) of at least one antibiotic compound. In some embodiments, the treatment solution comprises from about 0.1% to about 20% (w/v) of at least one antibiotic compound. In some embodiments, the treatment solution comprises from about 0.1% to about 5.0% (w/v) of at least one antibiotic compound. In some embodiments, the treatment solution comprises from about 0.25% to about 3.0% (w/v) of at least one antibiotic compound. In some embodiments, the treatment solution comprises about 1% (w/v) of at least one antibiotic compound. In some embodiments, the treatment solution comprises about 0.5% (w/v) of at least one antibiotic compound.

In some embodiments, the predetermined temperature ranges from about 2° C. to about 8° C. In some embodiments, the predetermined temperature is about 2° C., 3° C., 4° C., 5° C., 6° C., 7° C., or about 8° C. In some embodiments, the predetermined temperature is about 4° C.

In some embodiments, the fifth predetermined amount of time is about 24 hours or more. In some embodiments, the fifth predetermined amount of time is about 24 hours or more, or about 25 hours, or about 30, 36, 40, 48, 50, 55, 60, 65, 70, 72, 75, 80, 85, 90, 96, 100, 125, 150, 175, 200, 225, 250, 275, or about 300 hours or more. In some embodiments, the fifth predetermined amount of time ranges from about 24 hours to about 300 hours or more. In some embodiments, the fifth predetermined amount of time ranges from about 24 hours to about 170 hours or more. In some embodiments, the fifth predetermined amount of time ranges from about 24 hours to about 100 hours or more. In some embodiments, the fifth predetermined amount of time ranges from about 24 hours to about 72 hours or more. In some embodiments, the fifth predetermined amount of time ranges from about 24 hours to about 36 hours or more. In some embodiments, the fifth predetermined amount of time is about 24 hours or more. In some embodiments, the fifth predetermined amount of time is about 24 hours. In some embodiments, the fifth predetermined amount of time is about 36 hours or more. In some embodiments, the fifth predetermined amount of time is about 36 hours.

In some embodiments, the fish skin is statically immersed in a treatment solution comprising about 70% (w/v) or more glycol and from about 0.01% to about 30% (w/v) of at least one antibiotic compound, wherein the at least one antibiotic compound is a mixture of penicillin and streptomycin. In some embodiments, the fish skin is statically immersed in a treatment solution comprising about 70% (w/v) or more glycerol and from about 0.01% to about 30% (w/v) of at least one antibiotic compound, wherein the at least one antibiotic compound is a mixture of penicillin and streptomycin. In some embodiments, the fish skin is statically immersed in said treatment solution at 4° C. for at least 24 hours to form a processed fish skin.

After statically immersing the fish skin in a treatment solution at the predetermined temperature for a fifth predetermined amount of time, thereby forming a processed fish skin, the processed fish skin is packaged in a sealed package (step S222). In some embodiments, each individual package has a predetermined amount of shelf life if stored at predetermined conditions.

In some embodiments, the processed fish skin is packaged in a sealed package, wherein the sealed package comprises from about 20 mL to about 80 mL of a storage solution. In some embodiments, the processed fish skin is packaged in an individual vacuum sealed package comprising about 20 mL of a storage solution, or about 25 mL, 30 mL, 35 mL, 40 mL, 45 mL, 50 mL, 55 mL, 60 mL, 65 mL, 70 mL, 75 mL, or about 80 mL of a storage solution. In some embodiments, the processed fish skin is packaged in an individual vacuum sealed package comprising from about 25 mL to about 80 mL of a storage solution. In some embodiments, the processed fish skin is packaged in an individual vacuum sealed package comprising from about 30 mL to about 80 mL of a storage solution. In some embodiments, the processed fish skin is packaged in an individual vacuum sealed package comprising from about 40 mL to about 80 mL of a storage solution. In some embodiments, the processed fish skin is packaged in an individual vacuum sealed package comprising from about 40 mL to about 70 mL of a storage solution. In some embodiments, the processed fish skin is packaged in an individual vacuum sealed package comprising from about 40 mL to about 60 mL of a storage solution. In some embodiments, the processed fish skin is packaged in an individual vacuum sealed package comprising from about 40 mL to about 50 mL of a storage solution. In some embodiments, the processed fish skin is packaged in an individual vacuum sealed package comprising about 40 mL of a storage solution. In some embodiments, the processed fish skin is packaged in an individual vacuum sealed package comprising no more than 80 mL of a storage solution.

In some embodiments, the storage solution has antimicrobial properties as well as humectant properties. In some embodiments, the storage solution comprises a non-aqueous solvent, such as, for example, an alcohol (e.g., methanol, ethanol, propanol, isopropanol, butanol, t-butanol, etc.), glycerol, dimethyl sulfoxide (DMSO), a glycol (e.g., ethylene glycol, propylene glycol, etc.), or mixtures thereof. In some embodiments, the storage solution comprises non-aqueous solvent (e.g., ethanol, glycerol, DMSO, ethylene glycol, propylene glycol, etc.) and one or more of the following: an antibiotic compound, an antiviral agent, an antimycotic agent, chlorine dioxide, a detergent, antimicrobials, antifungal agents, hydrogen peroxide, sodium hydroxide, peracetic acid, or mixtures thereof. The glycerol may act as a humectant and, thus, storage solutions comprising glycerol may assist in softening or moisturizing the packaged processed fish skin. In some embodiments, the storage solution comprises glycerol, glycol (e.g., ethylene glycol, propylene glycol, etc.), ethanol, isopropanol, DMSO, an antibiotic compound, antifungal agents, hydrogen peroxide, peracetic acid, or mixtures thereof. In some embodiments, the storage solution comprises glycerol, glycol, ethanol, at least one antibiotic compound, hydrogen peroxide, peracetic acid, or mixtures thereof. In some embodiments, the storage solution comprises glycerol, ethanol, at least one antibiotic compound, peracetic acid, or mixtures thereof. In some embodiments, the storage solution comprises glycerol, ethanol, penicillin, vancomycin, streptomycin, gentamycin, kanamycin, neomycin, peracetic acid, or mixtures thereof. In some embodiments, the storage solution comprises glycerol. In some embodiments, the storage solution comprises glycerol and at least one antibiotic compound. In some embodiments, the storage solution comprises glycerol and penicillin. In some embodiments, the storage solution comprises ethanol. In some embodiments, the storage solution comprises peracetic acid.

In some embodiments, the method further comprises at least one of the following additional steps: a) dynamically immersing the fish skin for at least 30 minutes in the disinfectant solution after step ii); b) dynamically immersing the fish skin for at least 30 minutes in the first rinse solution after step iii); c) dynamically immersing the fish skin for at least 30 minutes in the first dehydration solution after step iv); d) dynamically immersing the fish skin for at least 30 minutes in the second dehydration solution after step v); e) dynamically immersing the fish skin for at least 30 minutes in the second rinse solution after step vi); and/or f) dynamically immersing the processed fish skin for at least 30 minutes in the treatment solution after step vii).

In some embodiments, the method for preparing the fish skin biological bandage comprises i) harvesting fish skin from a fish; ii) statically immersing the fish skin in a disinfectant solution for a first predetermined amount of time, then dynamically immersing the fish skin for at least 30 minutes in the disinfectant solution; iii) contacting the fish skin with a first rinse solution, then dynamically immersing the fish skin for at least 30 minutes in the first rinse solution; iv) statically immersing the fish skin in a first dehydration solution for a second predetermined amount of time, then dynamically immersing the fish skin for at least 30 minutes in the first dehydration solution; v) statically immersing the fish skin in a second dehydration solution at a predetermined temperature for a third predetermined amount of time, then dynamically immersing the fish skin for at least 30 minutes in the second dehydration solution; vi) statically immersing the fish skin in a second rinse solution for a fourth predetermined amount of time, then dynamically immersing the fish skin for at least 30 minutes in the second rinse solution; vii) statically immersing the fish skin in a treatment solution at the predetermined temperature for a fifth predetermined amount of time to form a processed fish skin, then dynamically immersing the processed fish skin for at least 30 minutes in the treatment solution; and viii) packaging the processed fish skin in a sealed package.

In some embodiments, the method for preparing the fish skin biological bandage comprises i) harvesting fish skin from a fish; ii) statically immersing the fish skin in a disinfectant solution comprising about 0.5% to about 2.0% (w/v) chlorhexidine for about 60 minutes or less; iii) contacting the fish skin with a first rinse solution comprising about 0.45% to about 7.2% (w/v) saline; iv) statically immersing the fish skin in a first dehydration solution comprising a mixture of a glycerol solution and a saline solution at a volume ratio of 75/25 for 60 minutes or less, wherein the glycerol solution comprises about 80% to about 99.5% (w/v) glycerol and the saline solution comprises from about 0.45% to about 7.2% (w/v) saline; v) statically immersing the fish skin in a second dehydration solution comprising about 80% to about 99.5% (w/v) glycerol at 4° C. for about 24 hours; vi) statically immersing the fish skin in a second rinse solution comprising about 0.45% to about 7.2% (w/v) saline for about 15 minutes or less; vii) statically immersing the fish skin in a treatment solution comprising about 80% to about 99.9% (w/v) glycerol and about 0.1% to about 20% (w/v) penicillin and streptomycin at 4° C. for at least 24 hours to form a processed fish skin; and viii) packaging the processed fish skin in an individual vacuum sealed package, wherein the package comprises 80 mL or less of a storage solution comprising glycerol, at least one antibiotic compound, ethanol, peracetic acid, or mixtures thereof.

In some embodiments, the method for preparing the fish skin biological bandage comprises i) harvesting fish skin from a fish; ii) statically immersing the fish skin in a disinfectant solution comprising about 0.5% to about 2.0% (w/v) chlorhexidine for about 60 minutes or less, then dynamically immersing the fish skin for at least 30 minutes in the disinfectant solution; iii) contacting the fish skin with a first rinse solution comprising about 0.45% to about 7.2% (w/v) saline, then dynamically immersing the fish skin for at least 30 minutes in the first rinse solution; iv) statically immersing the fish skin in a first dehydration solution comprising a mixture of a glycerol solution and a saline solution at a volume ratio of 75/25 for 60 minutes or less, wherein the glycerol solution comprises about 80% to about 99.5% (w/v) glycerol and the saline solution comprises from about 0.45% to about 7.2% (w/v) saline, then dynamically immersing the fish skin for at least 30 minutes in the first dehydration solution; v) statically immersing the fish skin in a second dehydration solution comprising about 80% to about 99.5% (w/v) glycerol at 4° C. for about 24 hours, then dynamically immersing the fish skin for at least 30 minutes in the second dehydration solution; vi) statically immersing the fish skin in a second rinse solution comprising about 0.45% to about 7.2% (w/v) saline for about 15 minutes or less, then dynamically immersing the fish skin for at least 30 minutes in the second rinse solution; vii) statically immersing the fish skin in a treatment solution comprising about 80% to about 99.9% (w/v) glycerol and about 0.1% to about 20% (w/v) penicillin and streptomycin at 4° C. for at least 24 hours to form a processed fish skin, then dynamically immersing the processed fish skin for at least 30 minutes in the treatment solution; and viii) packaging the processed fish skin in an individual vacuum sealed package, wherein the package comprises 80 mL or less of a storage solution comprising glycerol, at least one antibiotic compound, ethanol, peracetic acid, or mixtures thereof.

Alternatively, rather than or in addition to, packaging the processed fish skin in an individual vacuum sealed package comprising a storage solution, the processed fish skin can be cryopreserved and/or exposed to irradiation, such as E-beam irradiation or radio wave irradiation. In some embodiments, the processed fish skin is not cryopreserved or exposed to irradiation.

In some embodiments, the processed fish skin can be cryopreserved. In some embodiments, cryopreservation can involve immersing the processed fish skin in a cryoprotectant solution prior to freezing. In some embodiments, the cryoprotectant solution comprises an appropriate buffer, one or more cryoprotectants, and optionally a solvent, e.g. an organic solvent which in combination with water undergoes minimal expansion and contraction. Examples of cryoprotectants include sucrose, raffinose, dextran, trehalose, dimethylacetamide, DMSO, ethylene glycol, glycerol, propylene glycol, 2-methyl-2,4-pentanediol, ethanol, peracetic acid, certain antifreeze proteins and peptides, and combinations thereof. In some embodiments, the processed fish skin can optionally be frozen in a buffer solution that does not include cryoprotectants. In some embodiments, cryopreservation is performed at a pH of at least 5.5, such as 6.0, 6.5, 7.0, 7.5, 8.0, 8.5, 9.0, 9.5, 10.0 or more. In some embodiments the pH is between 7.0 and 9.0, e.g. between 7.5 and 8.5.

In some embodiments, the processed fish skin can be packaged inside a sterile container for cryopreservation, such as a glass vial or a pouch. In some embodiments, a TYVEK® pouch is used. For example, the processed fish skin can be incubated in a cryoprotectant solution, packaged in a TYVEK® pouch, then placed into a freeze dryer and frozen at a rate which is compatible with the cryoprotectant.

In some embodiments, the processed fish skin can be exposed to irradiation, such as E-beam irradiation or radio wave irradiation. In some embodiments, the processed fish skin can be immersed in an irradiation protective solution effective to stabilize the processed fish skin during and after exposure to irradiation. In some embodiments, the processed fish skin is exposed to an irradiation dose effective to sterilize the processed fish skin.

In some embodiments, the irradiation includes E-beam irradiation. In some embodiments, the radiation includes radio wave irradiation. In some embodiments, the radiation is provided at a dose sufficient to sterilize the processed fish skin after immersing the processed fish skin in an irradiation protective solution. In some embodiments, the irradiation protective solution comprises sucrose, raffinose, dextran, trehalose, dimethylacetamide, DMSO, ethylene glycol, glycerol, propylene glycol, 2-methyl-2,4-pentanediol, ethanol, peracetic acid, or combinations thereof. In some embodiments, the radiation is at a dose that is low enough to prevent damage to the processed fish skin.

E-beam radiation is a form of ionizing energy that is generally characterized by its low penetration and high dosage rates. The beam, a concentrated, highly charged stream of electrons, is generated by the acceleration and conversion of electricity. The electrons are generated by equipment referred to as accelerators, which are capable of producing beams that are either pulsed or continuous. As the product/material being sterilized passes beneath or in front of the electron beam, energy from the electrons is absorbed. This absorption of energy alters various chemical and biological bonds within the product/material. The energy that is absorbed is referred to as the "absorbed dose." A variety of E-beam irradiators can be used in the methods described herein and are commercially available, e.g., the RHODOTRON TT300 (from IBA, Louvain-la-Neuve, France) and the AEB emitter (from AEB, Willington, Mass.).

In some embodiments, a processed fish skin can be exposed to low-dose E-beam irradiation for a time and in an amount sufficient to achieve sterilization. The dosage of E-beam irradiation required to sterilize a processed fish skin can vary based on, e.g., the size of the processed fish skin, the type of processed fish skin, and the type and amount of microbial contaminant in, or suspected of being present in, the processed fish skin.

In some embodiments, a processed fish skin can be subjected to a one-sided exposure of the electron beam until a sterilizing dose of radiation is absorbed. An "absorbed dose" of radiation is expressed in terms of kilograys (kGy), wherein one kilogray is equal to one thousand joules of energy deposited per kilogram of material. For example, the processed fish skin can be irradiated until an absorbed dose of about 6 kGy or more (e.g., 7 kGy, 8 kGy, 9 kGy, 10, kGy, 12 kGy, 15 kGy, 20 kGy, 22 kGy, 25 kGy, 27 kGy, or up to 30 kGy, or fractional values of the foregoing) is achieved. In some embodiments, a processed fish skin can be exposed to irradiation until an absorbed dosage of about 6 kGy to about 30 kGy, about 10 kGy to about 15 kGy, or about 10 kGy to about 20 kGy is achieved.

E-beam or radio wave irradiation of a processed fish skin can be carried out, e.g., by placing the processed fish skin in a suitable container, e.g., a glass or plastic container, and exposing the processed fish skin to the radiation. For example, the processed fish skin may be placed on a conveyor, which then passes through the electron beam or is exposed to the radio wave source. The time of exposure to the radiation can be proportional to the dimensions of the processed fish skin.

Figure 3:
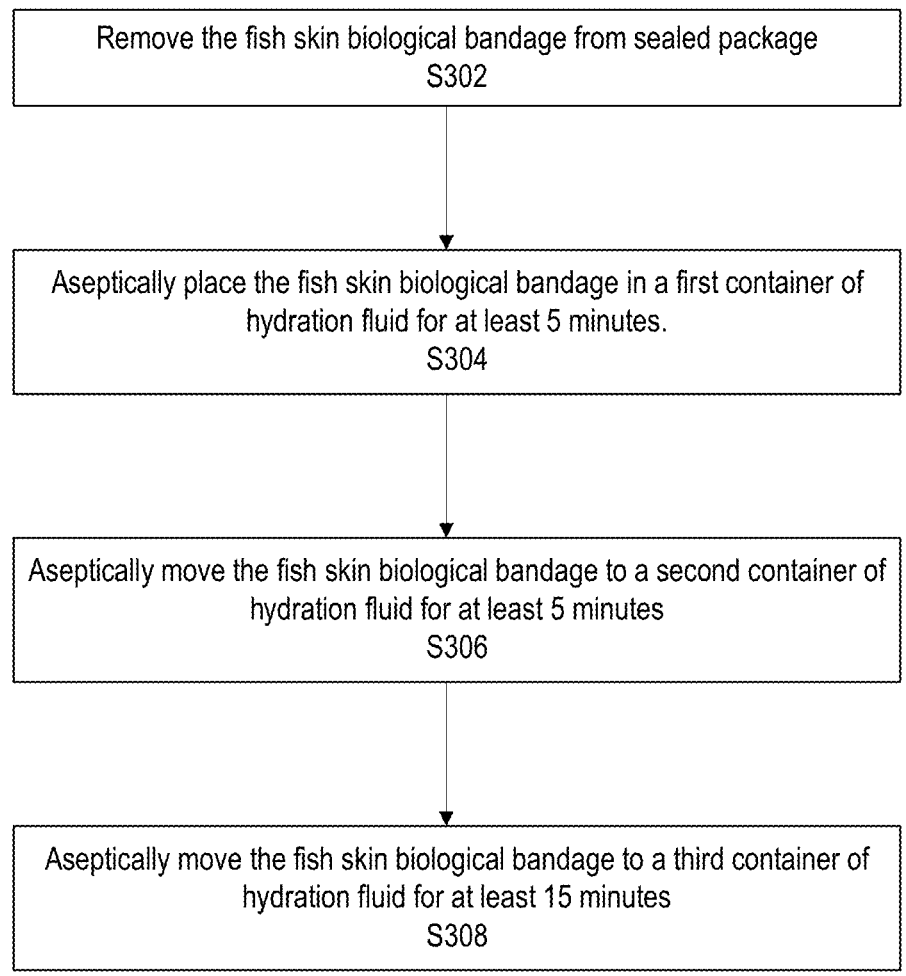
FIG. 3 illustrates an exemplary method for preparing a fish skin dressing for use in accordance with embodiments of the disclosure.

In some embodiments, after packaging the processed fish skin in an individual vacuum sealed package comprising a storage solution, the processed fish skin can be prepared for use as a biological bandage, as shown in FIG. 3. In some embodiments, prior to application on the wound, a fish skin biological bandage is removed from the sealed package (step S302) and re-hydrated according to the following exemplary process. The fish skin biological bandage is removed from sealed package and aseptically placed in a first container of hydration fluid (e.g. 0.9% saline) for a first predetermined amount of time (e.g. at least 5 minutes) (step S304). The bandage is aseptically removed from the first container and placed in a second container of hydration fluid (e.g. 0.9% saline) for a second predetermined amount of time (e.g. at least 5 minutes) (step S306). The bandage is aseptically removed from the second container and placed in a third container of hydration fluid (e.g. 0.9% saline) for a third predetermined amount of time (e.g. at least 15 minutes) prior to application on the wound (step S308). The dilution steps help to re-hydrate and soften the fish skin biological bandage that became too rigid for application on the wound in the sealed package. In some embodiments, if the processed fish skin was cryopreserved and/or exposed to irradiation, the processed fish skin can be prepared for use as a biological bandage according to the exemplary process steps described above.

II. PROCESSED FISH SKIN BIOLOGICAL BANDAGE

Typically, decellularized (or acellular) tissue materials have been used as biological bandages and/or allografts, autografts, and xenografts for patients with skin wounds. Decellularization of skin tissues is thought to eliminate immunologic responses and viral infections of the host, due to the removal of the cellular materials in the biological bandage material (e.g., surface antigens, DNA, bacteria, viruses, etc.). Decellularization of a graft material involves extracting the cellular materials from the extracellular matrix scaffold, leaving behind an acellular dermal matrix. As used herein, the term "decellularization" refers to the removal and/or extraction of cells and/or cellular components from a tissue. The phrase "cellular component," as used herein, refers to a whole cell (e.g., an epithelial cell), as well as the substances that constitute a portion of a cell, including cell membranes and macromolecules that are normally found enclosed within a cell membrane, embedded within a cell membrane, or attached to a cell membrane.

Figure 5:
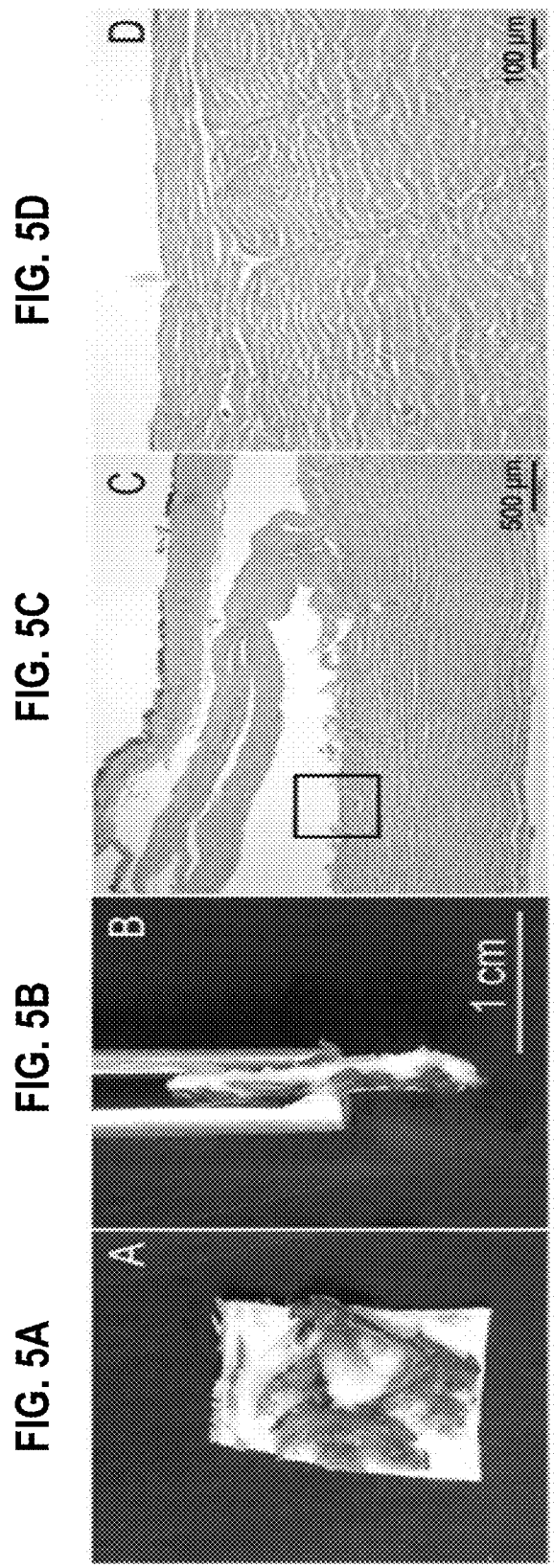
FIG. 5A shows a surface view of a processed tilapia skin biological bandage.
FIG. 5B shows a profile view of the processed tilapia skin biological bandage.
FIG. 5C shows the histopathology of the processed tilapia skin biological bandage.
FIG. 5D shows a view of the collagen dermal matrix in the processed tilapia skin biological bandage.

However, the methods used in the field to decellularize dermal tissue grafts involve several physical, chemical, and enzymatic treatments to yield acellular tissue grafts. Such treatments are not suitable for producing the sterile, pliable, and occlusive fish skin biological bandages described herein. As such, the processed fish skins for use as a biological bandage prepared according to the methods described herein will maintain a low cellular density or low cellularity. In other words, the processes for preparing the fish skin biological bandage described herein do not completely decellularize the fish skins. Thus, the fish skin biological bandages produced from the methods described herein contain a small amount of epithelial cells in addition to the collagen bundles within the processed fish skin dermis (FIGS. 5C and 5D). While the processed fish skin biological bandages described herein do contain some amount of cellular components (e.g., epithelial cells, DNA, etc.), these fish skin biological bandages are sterile and biocompatible.

The term "biocompatible" refers to a material that is substantially non-toxic in the in vivo environment of its intended use, and that is not rejected by the patient's physiological system (i.e., is non-antigenic). This can be assessed by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part 1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies treatment, surgery, or implantation of foreign objects into a living organism.

In some embodiments, the concentration of viable cellular components within the processed fish skin biological bandage is about 0.01% or more of that in the pre-processed fish skin. In some embodiments, the concentration of viable cellular components within the processed fish skin biological bandage is about 1% or more of that in the pre-processed fish skin. In some embodiments, the concentration of viable cellular components within the processed fish skin biological bandage is about 1% to about 90% of that in the pre-processed fish skin. In some embodiments, the concentration of viable cellular components within the processed fish skin biological bandage is about 1% of that in the pre-processed fish skin, or about 2%, 3%, 4%, 5%, 6%, 7%, 8%, 9%, 10%, 12%, 14%, 16%, 18%, 20%, 22%, 24%, 26%, 28%, 30%, 32%, 34%, 36%, 38%, 40%, 42%, 44%, 46%, 48%, 50%, 52%, 54%, 56%, 58%, 60%, 65%, 70%, 75%, 80%, 85%, or about 90% of that in the pre-processed fish skin. In some embodiments, the concentration of viable cellular components within the processed fish skin biological bandage is about 1% to about 80% of that in the pre-processed fish skin. In some embodiments, the concentration of viable cellular components within the processed fish skin biological bandage is about 5% to about 80% of that in the pre-processed fish skin. In some embodiments, the concentration of viable cellular components within the processed fish skin biological bandage is about 1% to about 70% of that in the pre-processed fish skin. In some embodiments, the concentration of viable cellular components within the processed fish skin biological bandage is about 5% to about 70% of that in the pre-processed fish skin.

In some embodiments, the concentration of viable cellular components within the processed fish skin biological bandage is about 1% to about 60% of that in the pre-processed fish skin. In some embodiments, the concentration of viable cellular components within the processed fish skin biological bandage is about 5% to about 60% of that in the pre-processed fish skin. In some embodiments, the concentration of viable cellular components within the processed fish skin biological bandage is about 1% to about 50% of that in the pre-processed fish skin. In some embodiments, the concentration of viable cellular components within the processed fish skin biological bandage is about 5% to about 50% of that in the pre-processed fish skin. In some embodiments, the concentration of viable cellular components within the processed fish skin biological bandage is about 1% to about 40% of that in the pre-processed fish skin. In some embodiments, the concentration of viable cellular components within the processed fish skin biological bandage is about 5% to about 40% of that in the pre-processed fish skin. In some embodiments, the concentration of viable cellular components within the processed fish skin biological bandage is about 1% to about 30% of that in the pre-processed fish skin. In some embodiments, the concentration of viable cellular components within the processed fish skin biological bandage is about 5% to about 30% of that in the pre-processed fish skin. In some embodiments, the concentration of viable cellular components within the processed fish skin biological bandage is about 1% to about 20% of that in the pre-processed fish skin. In some embodiments, the concentration of viable cellular components within the processed fish skin biological bandage is about 5% to about 20% of that in the pre-processed fish skin.

In some embodiments, the processed fish skin biological bandage comprises low cellularity compared to the cellularity of the pre-processed fish skin. As used herein, "low cellularity" refers to a low concentration of viable cellular components. For example, a processed fish skin biological bandage having low cellularity may have a concentration of viable cellular components that is about 0.01% to about 60% of that in the pre-processed fish skin. In some embodiments, the concentration of viable cellular components within the processed fish skin having low cellularity is about 1% to about 60% of that in the pre-processed fish skin. In some embodiments, the concentration of viable cellular components within the processed fish skin having low cellularity is about 0.01% to about 50% of that in the pre-processed fish skin. In some embodiments, the concentration of viable cellular components within the processed fish skin having low cellularity is about 1% to about 50% of that in the pre-processed fish skin. In some embodiments, the concentration of viable cellular components within the processed fish skin having low cellularity is about 0.01% to about 40% of that in the pre-processed fish skin. In some embodiments, the concentration of viable cellular components within the processed fish skin having low cellularity is about 1% to about 40% of that in the pre-processed fish skin. In some embodiments, the concentration of viable cellular components within the processed fish skin having low cellularity is about 0.01% to about 30% of that in the pre-processed fish skin. In some embodiments, the concentration of viable cellular components within the processed fish skin having low cellularity is about 1% to about 30% of that in the pre-processed fish skin. In some embodiments, the concentration of viable cellular components within the processed fish skin having low cellularity is about 0.01% to about 20% of that in the pre-processed fish skin. In some embodiments, the concentration of viable cellular components within the processed fish skin having low cellularity is about 1% to about 20% of that in the pre-processed fish skin. In some embodiments, the concentration of viable cellular components within the processed fish skin having low cellularity is about 0.01%, 0.05%, 0.1%, 0.25%, 0.5%, 0.75%, 1%, 2%, 3%, 4%, 5%, 6%, 7%, 8%, 9%, 10%, 11%, 12%, 13%, 14%, 15%, 16%, 17%, 18%, 19%, or about 20% of that in the pre-processed fish skin. In some embodiments, the concentration of viable cellular components within the processed fish skin having low cellularity is about 0.01% to about 15% of that in the pre-processed fish skin. In some embodiments, the concentration of viable cellular components within the processed fish skin having low cellularity is about 0.01% to about 10% of that in the pre-processed fish skin. In some embodiments, the concentration of viable cellular components within the processed fish skin having low cellularity is about 0.01% to about 5% of that in the pre-processed fish skin.

The concentration of viable cellular components or cellularity (e.g., epithelial cells and components thereof) in a fish skin (pre-processed and/or processed) can be expressed as "cell density," which is the total number of viable cells per unit area of fish skin surface. In some embodiments, the cell density of the processed fish skin biological bandage is between about 1 to about $1\times10^{10}$ cells/mm$^2$. In some embodiments, the cell density of the processed fish skin biological bandage is between about 1 to about $1\times10^9$ cells/mm$^2$. In some embodiments, the cell density of the processed fish skin biological bandage is between about 1 to about $1\times10^8$ cells/mm$^2$. In some embodiments, the cell density of the processed fish skin biological bandage is between about 1 to about $1\times10^7$ cells/mm$^2$. In some embodiments, the cell density of the processed fish skin biological bandage is between about 1 to about $1\times10^6$ cells/mm$^2$. In some embodiments, the cell density of the processed fish skin biological bandage is between about 1 to about $1\times10^5$ cells/mm$^2$. In some embodiments, the cell density of the processed fish skin biological bandage is between about 1 to about $1\times10^4$ cells/mm$^2$. In some embodiments, the cell density of the processed fish skin biological bandage is between about 1 to about 1000 cells/mm$^2$. In some embodiments, the cell density of the processed fish skin biological bandage is about 1 cell/mm$^2$, or about 2 cells/mm$^2$, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 275, 300, 350, 400, 450, 500, 550, 600, 650, 700, 750, 800, 850, 900, 950, or about 1000 cells/mm$^2$. Decellularization can be verified by, for example, testing the pre-processed and processed fish skins for DNA content. Removal of the nucleic acids from the processed fish skin can be determined, for example, by histological examination of the pre-processed and processed fish skins, and/or by a biochemical assay such as the PICOGREEN® assay, diphenylamine assay, or by PCR.

In some embodiments, the tensile strength of the processed fish skin will be sufficiently high to reflect the processed fish skin's resistance to tearing. In some embodiments, the tensile strength of the processed fish skin can be high enough to cause a suturing needle to bend. Tensile strength of the processed fish skin biological bandage can be assessed by determining the tensile stress at the maximum load to failure in Newtons (N), or put another way, the maximum load to failure normalized per cross-sectional area stress, measured in megapascals (MPa or N/mm$^2$). The processed fish skin biological bandage can be tested for tensile strength using a suitable testing system, such as, for example, an Instron tension/compression system, whereby the processed fish skin is clamped at either end and opposing forces are applied at a particular dislocation speed (e.g., 10 mm/min, 5 mm/min, etc.). The force at failure of the material is termed the "maximum load" or "maximum load to failure" (N). The maximum length the material can be elongated (i.e., stretched) until it breaks is termed "maximum extension" or "elongation at failure" (cm or mm). Percent strain (percent extension) is a measure of the deformation that occurs in a sample as the result of the externally applied load (e.g., how much the fish skin became stretched out or deformed performing elongation testing; the % change in length of the fish skin before and after stretching).

In some embodiments, the processed fish skins have a maximum load of about 20 N or more. In some embodiments, the processed fish skins have a maximum load of about 50 N or more. In some embodiments, the processed fish skins have a maximum load of about 50 N, 60 N, 70 N, 80 N, 90 N, 100 N, 200 N, 300 N, 400 N, 500 N, 1000 N, 5000 N, or about 10,000 N or more. In some embodiments, the processed fish skins have a maximum load of about 50 N to about 500 N. In some embodiments, the processed fish skins have a tensile strength of about 1 MPa or more. In some embodiments, the processed fish skins have a tensile strength of about 5 MPa or more. In some embodiments, the processed fish skins have a tensile strength of about 5 MPa, 6 MPa, 7 MPa, 8 MPa, 9 MPa, 10 MPa, 11 MPa, 12 MPa, 13 MPa, 14 MPa, 15 MPa, 16 MPa, 17 MPa, 18 MPa, 19 MPa, 20 MPa, 30 MPa, 40 MPa, 50 MPa, 100 MPa, 500 MPa, or about 1000 MPa or more. In some embodiments, the processed fish skins have a tensile strength of about 5 MPa to about 5000 MPa or more.

In some embodiments, the processed fish skins have a maximum extension of about 2.5 cm or more. In some embodiments, the processed fish skins have a maximum extension of about 3 cm or more. In some embodiments, the processed fish skins have a maximum extension of about 3 cm, 3.5 cm, 4.0 cm, 4.5 cm, 5.0 cm, 5.5 cm, 6.0 cm, 6.5 cm, 7.0 cm, 7.5 cm, 8.0 cm, 8.5 cm, 9.0 cm, 9.5, cm, or 10.0 cm or more. In some embodiments, the processed fish skins have a percent extension of about 10% or more. In some embodiments, the processed fish skins have a percent extension of about 15% or more. In some embodiments, the processed fish skins have a percent extension of about 20% or more. In some embodiments, the processed fish skins have a percent extension of about 25% or more. In some embodiments, the processed fish skins have a percent extension of about 30% or more. In some embodiments, the processed fish skins have a percent extension of about 30%, 35%, 40%, 45%, 50%, 55%, 60%, 65%, 70%, 75%, 80%, 85%, 90%, or about 95% or more.

In some embodiments, the processed fish skin biological bandage has a thickness of about 3 cm or less (i.e. in cross-section) (FIGS. 5A and 5B). In some embodiments, the processed fish skin biological bandage has a thickness of about 2 cm or less. In some embodiments, the processed fish skin biological bandage has a thickness of from about 0.1 mm to about 1.5 cm. In some embodiments, the processed fish skin biological bandage has a thickness of from about 0.1 mm to about 1.0 cm. In some embodiments, the processed fish skin biological bandage has a thickness of about 0.1 mm, or about 0.25 mm, 0.5 mm, 0.75 mm, 1.0 mm, 1.25 mm, 1.5 mm, 1.75 mm, 2.0 mm, 2.25 mm, 2.5 mm, 2.75 mm, 3.0 mm, 3.25 mm, 3.5 mm, 3.75 mm, 4.0 mm, 4.25 mm, 4.5 mm, 4.75 mm, 5.0 mm, 5.25 mm, 5.5 mm, 5.75 mm, 6.0 mm, 6.25 mm, 6.5 mm, 6.75 mm, 7.0 mm, 7.25 mm, 7.5 mm, 7.75 mm, 8.0 mm, 8.25 mm, 8.5 mm, 8.75 mm, 9.0 mm, 9.25 mm, 9.5 mm, 9.75 mm, or about 1.0 cm. The thickness can depend on a number of factors, such as the species of harvested fish.

III. APPLICATION OF BANDAGE ON THE SKIN

Also provided herein are methods for treating a site of a wound in a subject in need thereof, the method comprising applying to the site of the wound a processed fish skin biological bandage, thereby treating the site of the wound in the subject in need thereof. In some embodiments, the application of the processed fish skin biological bandage on the wound site of a subject in need thereof can promote pain relief at the would site; promote healing or regeneration of damaged or impaired tissue at the wound site; promote vascularization in regenerating tissue at the wound site; promote angiogenesis in regenerating tissue at the wound site; promote the growth of a vascularized tissue bed at the wound site; and/or promote the growth of supportive tissue at the wound site.

In some embodiments, the method for treating a wound site in a subject in need thereof comprises debriding or incising at least a portion of the wound site; and applying to the debrided or incised wound site a processed fish skin biological bandage, thereby treating the site of the wound in the subject in need thereof. In some embodiments, the processed fish skin biological bandage can be applied to the site of the wound on a patient with sutures. In some embodiments, the processed fish skin biological bandage can be applied to the site of the wound on a patient without sutures. The subject being treated with the processed fish skin biological bandage may not need to be administered immunosuppressants or pain relievers. Fish skin biological bandages according to various embodiments provide better pain control and promote pain relief, especially when compared to conventional bandages. Without wishing to be bound by theory, the healing properties of the collagen matrix within the fish skin biological bandages simultaneously provide additional protection against external factors by forming a viable barrier, providing a moist healing environment at the wound site and improved pain relief.

The term "wound" used herein refers broadly to a type of injury which damages a part or tissue of the body, for example, skin (e.g., epidermis, dermis, and hypodermis) and/or underlying tissue, mucous membrane (e.g., oral mucous membrane), or other epithelia (e.g., corneal epithelium). In other words, the term "wound" refers to injuries to the skin and subcutaneous tissue initiated in any one of a variety of ways (e.g., pressure sores from extended contact with saddles or collars, wounds induced by trauma, cuts, ulcers, burns and the like) and with varying characteristics. Different types of wounds include, for example, open wound, a chronic wound or non-healing wound, an acute wound, a burn wound, and a pressure wound. Wounds may classified into one of four grades depending on the depth of the wound: (i) Grade I: wounds limited to the epithelium; (ii) Grade II: wounds extending into the dermis; (iii) Grade III: wounds extending into the subcutaneous tissue; and (iv) Grade IV (or full-thickness wounds): wounds wherein bones are exposed (e.g., a bony pressure point such as the greater trochanter or the sacrum).

The term "partial thickness wound" refers to wounds that encompass Grades I-III; examples of partial thickness wounds include burn wounds, pressure sores, venous stasis ulcers, and diabetic ulcers. Pressure-inflicted skin conditions or pressure wounds, such as, for example, saddle sores on horses, collar sores on cats and dogs, or bedsores in human hospital patients, can occur when the skin is exposed to friction, moisture and a lack of oxygenation over an extended period of time. Under such conditions, irritation legions appear at the pressure points on the skin, such as the withers and girth of a horse or neck skin underlying a dog or cat's collar.

The terms "deep wound" or "full thickness wound" refer to wounds that encompass both Grade III and Grade IV wounds. Full thickness wounds comprise impairment or damage through the entire dermis, and into deeper underlying tissues, such as subcutaneous tissue, fascia, muscle tissue, tendon, nerve tissue, vascular tissue, visceral organs, and even bone or bone periosteum. Necrosis of effected tissues is common, as well as formation of eschar. In some cases, the site of a full thickness wound or injury may be painless, as a result of nerve tissue damage or destruction at the site. Loss of blood supply/blood flow is also common, and edema may be present.

An open wound refers to a type of injury in which a tissue, e.g., skin or mucous membrane, is torn, cut or punctured. Open wounds can be further classified according to the object that caused the wound. The types of open wound include, e.g., incisions or incised wounds, caused by a clean, sharp-edged object such as a knife, a razor or a glass splinter; lacerations, which are irregular tear-like wounds caused by some blunt trauma; abrasions (grazes), which are superficial wounds in which the topmost layer of the skin (the epidermis) is scraped off, often caused by a sliding fall onto a rough surface; puncture wounds, caused by an object puncturing the skin or mucous membrane, such as a nail or needle; penetration wounds, caused by an object such as a knife entering and coming out from the skin or mucous membrane; gunshot wounds (e.g., one at the site of entry and one at the site of exit), caused by a bullet or similar projectile driving into or through the body.

A chronic wound or non-healing wound is a wound that does not heal in an orderly and/or predictable amount of time (e.g., within three months). These wounds tend to prolong and/or halt healing time course, subjecting the wounds to further complications such as recurrent infections and necrosis. Chronic wounds may never heal or take years to heal, despite traditional treatment. Non-healing wounds may be wounds with increased amounts of bacteria. Examples of non-healing wounds include, but are not limited to, cracked nails, abscesses, lesions, ulcers, fissures, abscesses, and pressure sores/wounds.

In some cases, chronic/non-healing wounds can be associated with chronic diseases. The chronic disease can be the result of infection, e.g., bacterial infection, and the infection might no longer be present when the chronic disease or wound is treated. The symptoms of chronic diseases can sometimes be less severe than those of the acute phase of the same disease, but persist over a long period. Chronic diseases may be progressive, result in complete or partial disability, or even lead to death. Examples of chronic diseases that can be associated with non-healing wounds include a wound caused by chronic inflammation or bacterial species (e.g., an aerobic or facultative anaerobic gram positive and/or gram negative bacteria, sensitive and drug resistant bacteria, e.g., multi-drug resistant forms).

An acute wound is a wound wherein there is a balance between the production and degradation of molecules such as collagen (e.g., not substantially more degradation than production). Examples of acute wounds include, but are not limited to, incisions or incised wounds, caused by a clean, sharp-edged object such as a knife, a razor or a glass splinter; lacerations, which are irregular tear-like wounds caused by some blunt trauma; abrasions (grazes), which are superficial wounds in which the topmost layer of the skin (the epidermis) is scraped off, often caused by a sliding fall onto a rough surface; puncture wounds, caused by an object puncturing the skin or mucous membrane, such as a nail or needle; penetration wounds, caused by an object such as a knife entering and coming out from the skin or mucous membrane; gunshot wounds (e.g., one at the site of entry and one at the site of exit), caused by a bullet or similar projectile driving into or through the body.

A burn wound refers to a type of skin injury caused by heat (thermal), electricity, chemicals, or radiation. Burns can affect the skin (epidermal tissue and dermis) and/or deeper tissues, such as muscle, bone, and blood vessels. Burn injuries can be complicated by shock, infection, multiple organ dysfunction syndrome, electrolyte imbalance and respiratory distress. Burns can be classified as first-, second-, third-, or fourth-degree. First-degree burns can involve only the epidermis and be limited to redness (erythema), a white plaque and minor pain at the site of injury. For example, most sunburns are included as first-degree burns. Second-degree burns manifest as erythema with superficial blistering of the skin, and can involve more or less pain depending on the level of nerve involvement. Second-degree burns involve the superficial (papillary) dermis and may also involve the deep (reticular) dermis layer. Third-degree burns occur when the epidermis is lost with damage to the subcutaneous tissue. Burn victims will exhibit charring and severe damage of the epidermis, and sometimes hard eschar will be present. Third-degree burns result in scarring and victims will also exhibit the loss of hair shafts and keratin. Fourth-degree burns can damage muscle, tendon, and ligament tissue, thus result in charring and catastrophic damage of the hypodermis. In some instances the hypodermis tissue may be partially or completely burned away as well as this may result in a condition called compartment syndrome.

The burn depths are described as superficial, superficial partial-thickness, deep partial-thickness, or full-thickness. Burns can also be assessed in terms of total body surface area (TBSA), which is the percentage affected by partial thickness or full thickness burns (erythema/superficial thickness burns are not counted).

Thermal burns are by far the most common types of burns. Although the skin is usually the part of the body that is burned, the tissues under the skin can also be burned, and internal organs can be burned even when the skin is not. For example, drinking a very hot liquid or caustic substance such as acid can burn the esophagus and stomach. Inhaling smoke or hot air from a fire burn the lungs. When tissues are damaged by a burn, fluid may leak from blood vessels (capillary permeability), causing swelling or edema. In an extensive burn, loss of a large amount of fluid from abnormally leaky blood vessels can cause shock. In shock, blood pressure decreases so much that too little blood flows to the brain and other vital organs.

Electrical burns may be caused by a temperature of more than 9,000° F., generated by an electric current when it passes from the electrical source to the body. This type of burn, sometimes called an electrical arc burn, usually completely destroys and chars the skin at the current's point of entry into the body. Because the resistance (the body's ability to stop or slow the current's flow) is high where the skin touches the current's source, much of the electrical energy is converted into heat, thus burning the surface. Most electrical burns also severely damage the tissues under the skin, including fascia, muscle, tendon, nerve tissue, and bone. These burns vary in size and depth and may affect an area much larger than that indicated by the area of injured skin. Large electrical shocks can paralyze breathing and disturb heart rhythm, causing irregular heartbeats.

Chemical burns can be caused by various irritants and poisons, including strong acids and alkalis, phenols and cresols (organic solvents), mustard gas, and phosphorus. Chemical burns can cause tissue death that can slowly spread for hours after the burn.

Radiation burns can be caused by nuclear weapons, nuclear accidents, laboratory exposure, accidents during X-ray radiation chemotherapy, and over-exposure to sun. Radiation burns can cause inflammation, edema, ulcerations, damage to underlying endothelium and other cell types, as well as mutagenesis resulting in cancer, especially hematologic malignancies.

The processed fish skin biological bandage can be used to treat any and all types of wounds described above. For example, the processed fish skin biological bandages are suitable for application on burn wounds (full and partial thickness), acute wounds, pressure wounds, and chronic or non-healing wounds. When applied on such wounds, fish skin biological bandages provide improved antibacterial properties when compared to conventional bandages.

The patient or subject that can be treated using the processed fish skin biological bandages described herein can be a human or a non-human animal. Suitable human subjects include, for example, a human patient having a wound as described herein. Non-human animal subjects include all vertebrates, such as non-mammals (e.g., chickens, amphibians, reptiles, etc.) and mammals/non-human primates (e.g., elephant, sheep, dog, cat, cow, pig, etc.). Suitable animal subjects include, but are not limited to, wild animals, farm animals, zoo animals, circus animals, companion (pet) animals, and domesticated and/or agriculturally useful animals. In some embodiments, the subject in need thereof is a non-human animal. In some embodiments, the subject is a primate, rodent, or bird. In some embodiments, the subject in need thereof can be a rhinoceros, elephant, tapir, guinea pig, hamster, gerbil, rat, mouse, rabbit, dog, fox, wolf, cat, bobcat, mountain lion, bear, pony, horse, pig, sheep, cow, goat, deer, llama, alpaca, rhesus monkey, monkey, tamarind, ape, baboon, gorilla, chimpanzee, orangutan, gibbon, koi fish, tortoise, fowl, pheasant, quail (or other gamebirds), waterfowl, ostrich, chicken, turkey, duck, goose, free flying bird, owl, hawk, or eagle. In some embodiments, the subject in need thereof is selected from the group comprising bears, mountain lions, bobcats, foxes, ducks, rabbits, tortoises, pigs, horses, ponies, dogs, cats, owls, koi fish, or llamas.

Figure 4:
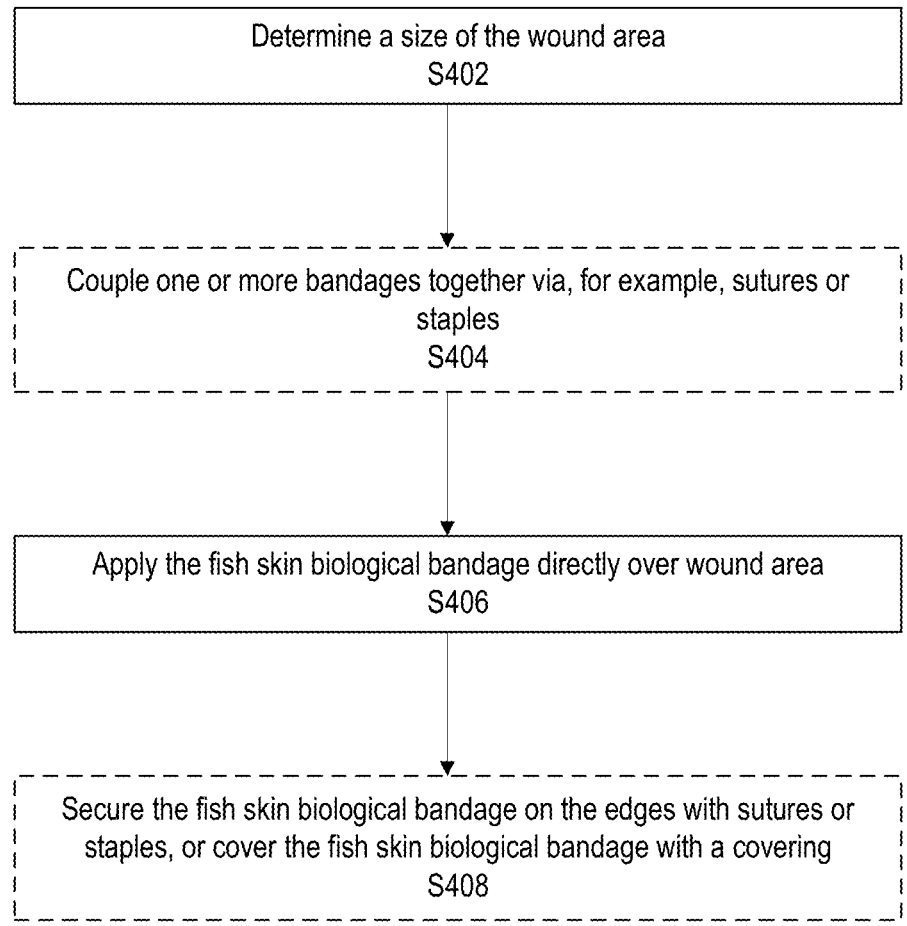
FIG. 4 illustrates an exemplary method for applying a fish skin dressing over a wound area in accordance with embodiments of the disclosure.

An exemplary process for applying the fish skin biological bandage on a wound is illustrated in FIG. 4. At first, a size of the wound area is determined (step S402). According to various embodiments, bandages can be coupled to each other, for example via sutures or staples, to cover a wound area that is larger than an individual bandage (step S404). Exemplary fish skin biological bandages discussed herein are applied directly over the wound area (step S406). The bandage can be secured on the edges with sutures or staples, or left in place and covered with a bandage depending on the application and/or the type of patient (step S408). For examples, sutures or staples may be more suitable for animals that are harder to keep a bandage, such as marine mammals.

Fish skin biological bandages discussed herein provide better protection than conventional bandages as they provide a better barrier for infection from external factors (e.g. dust) while keeping the wound moist to expedite the healing process. This property is beneficial for use of the fish skin biological bandages by military personnel, at non-sterile conditions. Moreover, since the wound is kept moist, the bandage is prevented from sticking to the dried secretions of the wound.

Moreover, the collagen structure of the bandages further improve the healing process by stimulating tissue growth at the wound area. Collagen in the fish skin biological bandage helps migrate numerous types of cells, including fibroblasts and keratinocytes, to the wound. These cells stimulate tissue growth at the wound area. In addition, the fish skin biological bandages according to embodiments provide substantial economic benefits over conventional biological bandages. For example, the cost to obtain and prepare a biological bandage of a predetermined size from human cadavers is about $3,000 while the cost to obtain and prepare a fish skin biological bandage of same size is about $50.

The above description is illustrative and is not restrictive. Many variations of the invention may become apparent to those skilled in the art upon review of the disclosure. The scope of the invention may, therefore, be determined not with reference to the above description, but instead may be determined with reference to the pending claims along with their full scope or equivalents.

One or more features from any embodiment may be combined with one or more features of any other embodiment without departing from the scope of the invention.

A recitation of "a", "an" or "the" is intended to mean "one or more" unless specifically indicated to the contrary.

As used herein, the terms "about" and "approximately equal" are used herein to modify a numerical value and indicate a defined range around that value. If "X" is the value, "about X" or "approximately equal to X" generally indicates a value from 0.90X to 1.10X. Any reference to "about X" indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%."

IV. EXAMPLES

The following examples are offered to illustrate, but not to limit, the claimed invention.

Example 1. Clinical Applications of the Fish Skin Biological Bandage

The following example describes the use of the fish skin biological bandages in veterinary medicine for treating severe burns and chronic non-healing wounds. These patients were suffering from either a severe burn wound or a non-healing wound, which would have typically resulted in increased chance of death or euthanasia. The following clinical case studies demonstrate the healing properties of the fish skin biological bandages described herein.

Figure 6:
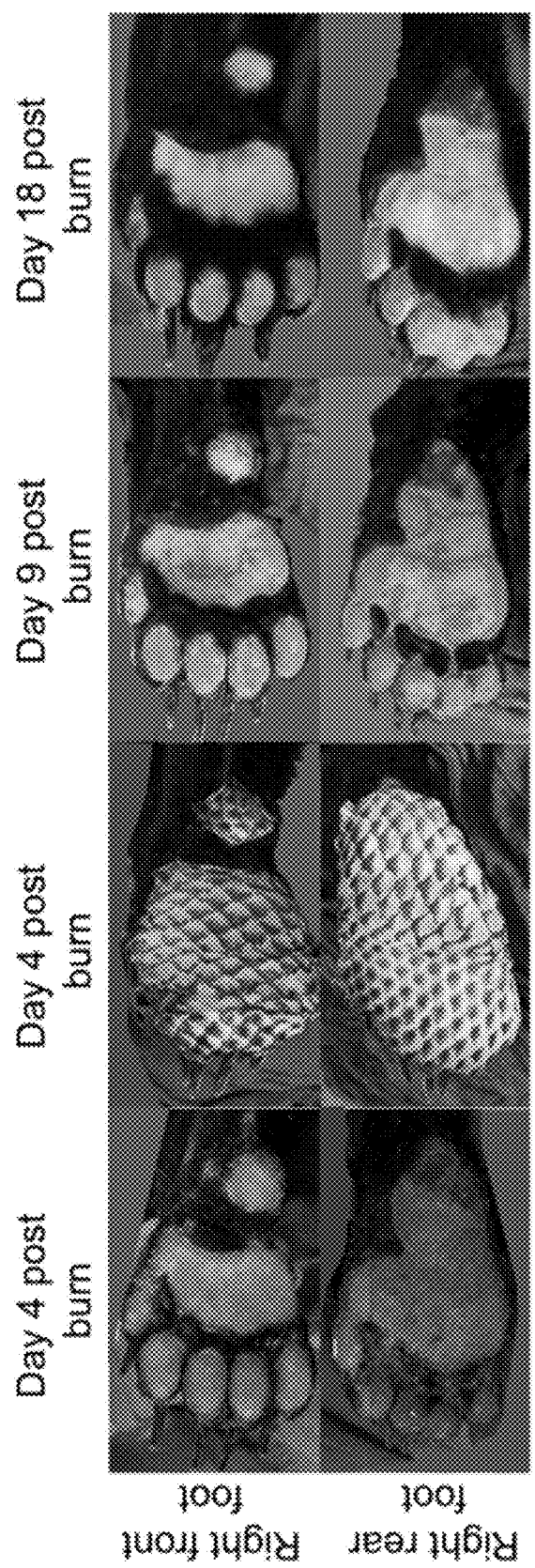
FIG. 6 shows a timeline of healing and epithelialization of black bear feet with full thickness thermal burns after treatment using the processed tilapia skin biological bandage.

Three bears (two adults and one juvenile) were presented with full thickness burns extending along their feet. These burns cause severe pain and would typically need 4-6 months for full healing. The fish skin biological bandages were prepared according to the methods described herein and were applied directly to the burn wounds, sutured in place, and no additional synthetic bandage material was needed. With the application of the fish skin biological bandages, the patients showed markedly improved pain control to the extent that they went from not walking prior to the application, to immediately walking on their paws after application. Decreased time to full wound healing was also noted (FIG. 6) and all the animals were released successfully back to the wild within 4-6 weeks, which was a drastic contrast to the standard healing time of 4-6 months.

In addition, the bandages have been applied to non-healing wounds in barn owls. One of the owls had a full thickness leg wound that, despite other wound care applications, had not healed in over two months. This resulted in his continued captivity and cage confinement. After applying the fish skin bandages, his wound healed within two weeks and he was released for flight conditioning in the aviary, and later successfully released back into the wild.

The clinical effectiveness in relieving pain and improved time for healing has also been demonstrated in other types of burns, such as chemical burns. An 18-month old cob pony was treated for suspected acid burns to her face resulting in the loss of skin along the entire length of her head. To help with her pain, she was on several continuous pain medications, but her heart rate remained high and she would not allow the lightest touch to her face. Due to the severe pain and length of time to heal, humane euthanasia was considered. In an attempt to help her, the processed fish skin biological bandages prepared using the methods described herein were placed on the entire wound area extending along her eyelids, nose, and muzzle. The bandages were sutured in place and then covered with a secondary bandage. Immediately after placement, she started to eat and by the following morning the additional pain medications were decreased or discontinued entirely. Her heart rate returned to normal and she would allow examination of her face. She continued to improve and with 3 days visible new skin was present (FIGS. 7A-7F). She went on to fully recover.

What is claimed is:

1. A method for preparing a fish skin biological bandage comprising:
   i) harvesting fish skin from a fish;
   ii) statically immersing the fish skin in a disinfectant solution for a first predetermined amount of time;
   iii) contacting the fish skin with a first rinse solution;
   iv) statically immersing the fish skin in a first dehydration solution for a second predetermined amount of time;
   v) statically immersing the fish skin in a second dehydration solution at a predetermined temperature for a third predetermined amount of time;
   vi) statically immersing the fish skin in a second rinse solution for a fourth predetermined amount of time;
   vii) statically immersing the fish skin in a treatment solution at the predetermined temperature for a fifth predetermined amount of time to form a processed fish skin; and
   viii) packaging the processed fish skin in a sealed package.

2. The method of claim 1, wherein the disinfectant solution comprises chlorhexidine, wherein the chlorhexidine is present in an amount ranging from about 0.1% to about 3.0% (w/v).

3. The method of claim 1, wherein the first predetermined amount of time and the second predetermined amount of time is about 120 minutes or less.

4. The method of claim 1, wherein the first rinse solution and the second rinse solution comprise saline, wherein the saline is present in an amount ranging from about 0.25% to about 8.0% (w/v).

5. The method of claim 1, wherein in step iii) contacting the fish skin with the first rinse solution further comprises:
   a) rinsing the fish skin with the first rinse solution; and/or
   b) statically immersing the fish skin in the first rinse solution.

6. The method of claim 1, wherein the first dehydration solution comprises a mixture of a glycerol solution and a saline solution at a volume ratio of 75/25, wherein the glycerol solution comprises from about 80% to about 100% (w/v) glycerol and the saline solution comprises from about 0.25% to about 8.0% (w/v) saline.

7. The method of claim 1, wherein the second dehydration solution comprises glycerol, wherein the glycerol is present in an amount of about 80% (w/v) or more.

8. The method of claim 1, wherein the predetermined temperature ranges from about 2° C. to about 8° C.

9. The method of claim 1, wherein the third predetermined amount of time is about 48 hours or less.

10. The method of claim 1, wherein the fourth predetermined amount of time is about 30 minutes or less.

11. The method of claim 1, wherein the fifth predetermined amount of time is about 24 hours or more.

12. The method of claim 1, wherein the treatment solution comprises glycerol and at least one antibiotic compound, wherein the glycerol is present in an amount of about 70% (w/v) or more and the at least one antibiotic compound is present in an amount ranging from about 0.01% to about 30% (w/v).

13. The method of claim 12, wherein the at least one antibiotic compound is selected from the group consisting of penicillin, streptomycin, and mixtures thereof.

14. The method of claim 1, wherein the sealed package comprises about 40 mL to about 80 mL of a storage solution.

15. The method of claim 14, wherein the storage solution is glycerol.

16. The method of claim 1, wherein the fish skin is harvested within 24 hours of death of the fish.

17. The method of claim 1, further comprising repeating the steps of:
   ii) statically immersing the fish skin in a disinfectant solution for a first predetermined amount of time; and
   iii) contacting the fish skin with a first rinse solution, wherein steps ii) and iii) are repeated at least once and before performing step iv).

18. The method of claim 1, wherein the fish is selected from the group consisting of salmon, tuna, tilapia, and trout.

19. The method of claim 1, further comprising at least one of the following additional steps selected from the group consisting of:
   a) dynamically immersing the fish skin for at least 30 minutes in the disinfectant solution after step ii);
   b) dynamically immersing the fish skin for at least 30 minutes in the first rinse solution after step iii);
   c) dynamically immersing the fish skin for at least 30 minutes in the first dehydration solution after step iv);
   d) dynamically immersing the fish skin for at least 30 minutes in the second dehydration solution after step v);
   e) dynamically immersing the fish skin for at least 30 minutes in the second rinse solution after step vi); and
   f) dynamically immersing the processed fish skin for at least 30 minutes in the treatment solution after step vii).

20. A method for preparing a fish skin biological bandage comprising:
   i) harvesting fish skin from a fish;
   ii) statically immersing the fish skin in a disinfectant solution comprising about 0.5% to about 2.0% (w/v) chlorhexidine for about 60 minutes or less;
   iii) contacting the fish skin with a first rinse solution comprising about 0.45% to about 7.2% (w/v) saline;
   iv) statically immersing the fish skin in a first dehydration solution comprising a mixture of a glycerol solution and a saline solution at a volume ratio of 75/25 for 60 minutes or less, wherein the glycerol solution comprises about 80% to about 99.5% (w/v) glycerol and the saline solution comprises from about 0.45% to about 7.2% (w/v) saline;
   v) statically immersing the fish skin in a second dehydration solution comprising about 80% to about 99.5% (w/v) glycerol at 4° C. for about 24 hours;
   vi) statically immersing the fish skin in a second rinse solution comprising about 0.45% to about 7.2% (w/v) saline for about 15 minutes or less;
   vii) statically immersing the fish skin in a treatment solution comprising about 80% to about 99.9% (w/v) glycerol and about 0.1% to about 20% (w/v) penicillin and streptomycin at 4° C. for at least 24 hours to form a processed fish skin; and
   viii) packaging the processed fish skin in an individual vacuum sealed package, wherein the package comprises 80 mL or less of a storage solution.

21. The method of claim 14, wherein the storage solution is at least one antibiotic compound.

22. The method of claim 14, wherein the storage solution is ethanol.

23. The method of claim 14, wherein the storage solution is peracetic acid.

24. The method of claim 20, wherein the storage solution is glycerol.

25. The method of claim 20, wherein the storage solution is at least one antibiotic compound.

26. The method of claim 20, wherein the storage solution is ethanol.

27. The method of claim 20, wherein the storage solution is peracetic acid.

* * * * *